(12) United States Patent
Sun et al.

(10) Patent No.: US 10,703,770 B2
(45) Date of Patent: Jul. 7, 2020

(54) COMPOSITIONS AND METHODS FOR THE DISSOLUTION AND DEPOLYMERIZATION OF LIGNIN

(71) Applicant: National Technology & Engineering Solutions of Sandia, LLC, Albuquerque, NM (US)

(72) Inventors: Jian Sun, Albany, CA (US); Tanmoy Dutta, Berkeley, CA (US); Parthasarathi Ramakrishnan, Fremont, CA (US); Blake A. Simmons, San Francisco, CA (US); Seema Singh, Mountain House, CA (US)

(73) Assignee: National Technology & Engineering Solutions of Sandia, LLC, Albuquerque, NM (US)

( * ) Notice: Subject to any disclaimer, the term of this patent is extended or adjusted under 35 U.S.C. 154(b) by 0 days.

(21) Appl. No.: 15/615,777

(22) Filed: Jun. 6, 2017

(65) Prior Publication Data
US 2017/0349617 A1     Dec. 7, 2017

Related U.S. Application Data

(60) Provisional application No. 62/346,351, filed on Jun. 6, 2016.

(51) Int. Cl.
*C07G 1/00* (2011.01)
*C12P 19/02* (2006.01)
(Continued)

(52) U.S. Cl.
CPC .............. *C07G 1/00* (2013.01); *C12P 7/10* (2013.01); *C12P 7/14* (2013.01); *C12P 19/02* (2013.01);
(Continued)

(58) Field of Classification Search
CPC .......................................... C07G 1/00
See application file for complete search history.

(56) References Cited

U.S. PATENT DOCUMENTS

| | | | |
|---|---|---|---|
| 9,562,160 B2* | 2/2017 | Powell | D21C 3/20 |
| 2013/0130328 A1* | 5/2013 | Tabata | C12P 7/06 |
| | | | 435/99 |
| 2014/0249300 A1* | 9/2014 | Bozell | C07G 1/00 |
| | | | 530/507 |

OTHER PUBLICATIONS

Prado, R. et al. "Lignin oxidation and depolymerisation in ionic liquids" Green Chem., 2016, 18, 834-841; Published on Sep. 21, 2015 (Year: 2015).*

(Continued)

*Primary Examiner* — Medhanit W Bahta
(74) *Attorney, Agent, or Firm* — Robin C. Chiang; Lawrence Berkeley National Laboratory

(57) ABSTRACT

The present invention provides for a method for dissolving and/or depolymerizing lignin comprising: (a) providing a composition comprising lignin, (b) contacting the composition with a strong hydrogen donor, such as a polyol, to form a first solution, (c) incubating the first solution at a temperature equal to or less than 100° C., whereby at least 20% by weight of the lignin is dissolved, (d) optionally introducing an oxidation agent to the first solution to form a second solution, wherein the temperature of the second solution is equal to or less than 100° C., whereby lignin is depolymerized, and (e) optionally introducing an anti-solvent to the second solution to precipitate the depolymerized lignin.

15 Claims, 16 Drawing Sheets

(51) Int. Cl.
 C12P 7/10 (2006.01)
 C12P 7/14 (2006.01)
(52) U.S. Cl.
 CPC ... *C12Y 302/01004* (2013.01); *C12P 2201/00* (2013.01)

(56) References Cited

OTHER PUBLICATIONS

Wang et al., "Ionic liquid processing of cellulose." Chemical Society Reviews, vol. 41, pp. 1519-1537 (2012).
Mosier et al., "Features of promising technologies for pretreatment of lignocellulosic biomass." Bioresource Technol, vol. 96, pp. 673-686 (2005).
Hallett et al., "Room-Temperature Ionic Liquids: Solvents for Synthesis and Catalysis. 2." Chemical Reviews, vol. 111, pp. 3508-3576 (2011).
Shi et al., "Impact of mixed feedstocks and feedstock densification on ionic liquid pretreatment efficiency." Biofuels vol. 4, No. 1, pp. 63-72 (2014).
Li et al., "Scale-up and evaluation of high solid ionic liquid pretreatment and enzymatic hydrolysis of switchgrass." DOI: 10.1186/1754-6834-6-154. Biotechnol Biofuels., vol. 6, p. 154 (2013).
daSilva et al., "Continuous pretreatment of sugarcane bagasse at high loading in an ionic liquid using a twin-screw extruder" Green Chemistry, vol. 15, pp. 1991-2001 (2013).
Shi et al., "One-pot ionic liquid pretreatment and saccharification of switchgrass." Green Chem, vol. 15, pp. 2579-2589 (2013).
Sun et al., "Understanding pretreatment efficacy of four cholinium and imidazolium ionic liquids by chemistry and computation." Green Chem, 2014, vol. 16, pp. 2546-2557 (2014).
Kurnia et al., "Thermophysical properties of hydroxyl ammonium ionic liquids." The Journal of Chemical Thermodynamics, vol. 41, pp. 517-521 (2009).
Greaves et al., "Protic Ionic Liquids: Solvents with Tunable Phase Behavior and PhysicoChemical Properties." J Phys Chem B, vol. 110, pp. 22479-22487 (2006).
Wada et al., "hermally Induced Crystal Transformation from Cellulose Iα to Iβ." Polym J, vol. 5, pp. 155-159 (2003).
Cheng et al., "Transition of Cellulose Crystalline Structure and Surface Morphology of Biomass as a Function of Ionic Liquid Pretreatment and Its Relation to Enzymatic Hydrolysis." Biomacromolecules, vol. 12, pp. 933-941 (2011).
Remsing et al., "Mechanism of cellulose dissolution in the ionic liquid 1-n-butyl-3-methylimidazolium chloride: a 13C and 35/37Cl NMR relaxation study on model systems." DOI: 10.1039/B600586C (Communication). Chemical communications, pp. 1271-1273 (2006).
Wyman et al., "Ethanol Fundamentals of production from renewable feedstocks and use as a transportation fuel." Appl Biochem Biotech, vol. 24-5, No. 1, pp. 735-753 (1990).
Xu et al., "$CO_2$ enabled process integration for the production of cellulosic ethanol using bionic liquids." DOI: 10.1039/C6EE00913A (Paper). Energy & Environmental Science, vol. 9, pp. 2822-2834 (2016).
Cheng et al., "Theory, practice and prospects of X-ray and neutron scattering for lignocellulosic biomass characterization: towards understanding biomass pretreatment". Energy & Environmental Science, vol. 8, 436 (2015).
Pu et al, "Ionic Liquid as a Green Solvent for Lignin", Journal of Wood Chemistry and Technology, 27, 23 (2007).
Zivkovic et al, "Volumetric and Viscometric Behavior of Binary Systems 2-Butanol + PEG 200, + PEG 400, + Tetraethylene Glycol Dimethyl Ether, and + N-Methyl-2-pyrrolidone", Journal of Chemical and Engineering Data, 58, 3332 (2013).
Ji et al, "Mechanism of Lignin Dissolution and Regeneration in Ionic Liquid", Energy & Fuels, 26, 6393 (2012).
Singh et al, "Comparison of different biomass pretreatment techniques and their impact on chemistry and structure", Frontiers in Energy Research, 2 (2015).
Selig et al, "The Effect of Lignin Removal by Alkaline Peroxide Pretreatment on the Susceptibility of Corn Stover to Purified Cellulolytic and Xylanolytic Enzymes", Applied Biochemistry and Biotechnology, 155, 397 (2009).
Kirk et al, "Enzymatic 'combustion': The microbial degradation of lignin", Annual Reviews in Microbiology, 41, 465 (1987).
Zhu et al, "Electrochemical depolymerization of lignin into renewable aromatic compounds in a nondiaphragm electrolytic cell", Rsc Advances, 4, 6232 (2014).
Eriksson et al, Microbial and enzymatic degradation of wood and wood components, Springer Science & Business Media, 2012.
Higuchi, T., in New Trends in Research and Utilization of Solar Energy through Biological Systems, eds. H. Mislin and R. Bachofen, Birkhäuser Basel, Basel, 1982, pp. 87-94.
Brown et al, "Discovery and Characterization of Herne Enzymes from Unsequenced Bacteria: Application to Microbial Lignin Degradation", J Am Chem Soc, 133, 18006 (2011).
Bugg et al, "Pathways for degradation of lignin in bacteria and fungi", Nat Prod Rep, 28, 1883 (2011).

* cited by examiner

| | RMSD (Å) |
|---|---|
| Dilignol | - |
| Dilignol-EG$_1$ | 1.24 |
| Dilignol-EG$_3$ | 1.40 |
| Dilignol-EG$_1$-H$_2$O$_2$ | 1.51 |
| Dilignol-EG$_{10}$ | 5.70 |

COMPOSITIONS AND METHODS FOR THE DISSOLUTION AND DEPOLYMERIZATION OF LIGNIN

RELATED PATENT APPLICATIONS

The application claims priority to U.S. Provisional Patent Application Ser. No. 62/346,351, filed Jun. 6, 2016, which is herein incorporated by reference in its entirety.

STATEMENT OF GOVERNMENTAL SUPPORT

The invention was made with government support under Contract Nos. DE-AC02-05CH11231 awarded by the U.S. Department of Energy. The government has certain rights in the invention.

FIELD OF THE INVENTION

The present invention is in the field of depolymerization of lignin.

BACKGROUND OF THE INVENTION

Lignin is one of the most abundant biopolymers found in the planet earth. However, the residual lignin (20-30 wt % of the initial biomass) obtained after pretreatment is often overlooked as byproduct and in the paper and pulp industry and typically used for waste heat production. The structure of lignin suggests that it can be a valuable source of chemicals, particularly phenolics, which could significantly improve the economics of a biorefinery. Unfortunately depolymerization of lignin with selective bond cleavage is still the major challenge for converting it into value-added chemicals.

The current method on lignin pretreatment and depolymerization required sulfuric acid or alkali under much high temperature (e.g. 180° C.), which results in the main disadvantages of high-energy consumption and waste emission. Development of a simple, efficient and economic route to dissolve and depolymerize lignin is still a challenge.

SUMMARY OF THE INVENTION

The present invention provides for a method for dissolving and/or depolymerizing lignin comprising: (a) providing a composition comprising lignin, (b) contacting the composition with a strong hydrogen donor, such as a polyol, to form a first solution, (c) incubating the first solution at a temperature equal to or less than 100° C., whereby at least 20% by weight of the lignin is dissolved, (d) optionally introducing an oxidation agent to the first solution to form a second solution, wherein the temperature of the second solution is equal to or less than 100° C., whereby lignin is at least partly, substantially, or wholly depolymerized, and (e) optionally introducing an anti-solvent to the second solution to precipitate the depolymerized lignin.

The present invention provides for a composition and methods for depolymerizing lignin as described herein. The present invention provides a process in which higher loading lignin is dissolved at a lower temperature, and/or the dissolved lignin is depolymerized into lower molecular weight at a temperature as low as possible. In some embodiments, the above two processes are performed separately or coupled together at room temperature.

The present invention also provides for a method of pretreating biomass comprising contacting a biomass with a low toxic inexpensive protic ionic liquid (PIL) to form a solution, and optionally saccharifying or simultaneous saccharifying and fermenting the solution in the presence of an enzyme, such as a cellulase.

BRIEF DESCRIPTION OF THE DRAWINGS

The foregoing aspects and others will be readily appreciated by the skilled artisan from the following description of illustrative embodiments when read in conjunction with the accompanying drawings.

BRIEF DESCRIPTION OF THE DRAWINGS

The foregoing aspects and others will be readily appreciated by the skilled artisan from the following description of illustrative embodiments when read in conjunction with the accompanying drawings.

Figure 1:
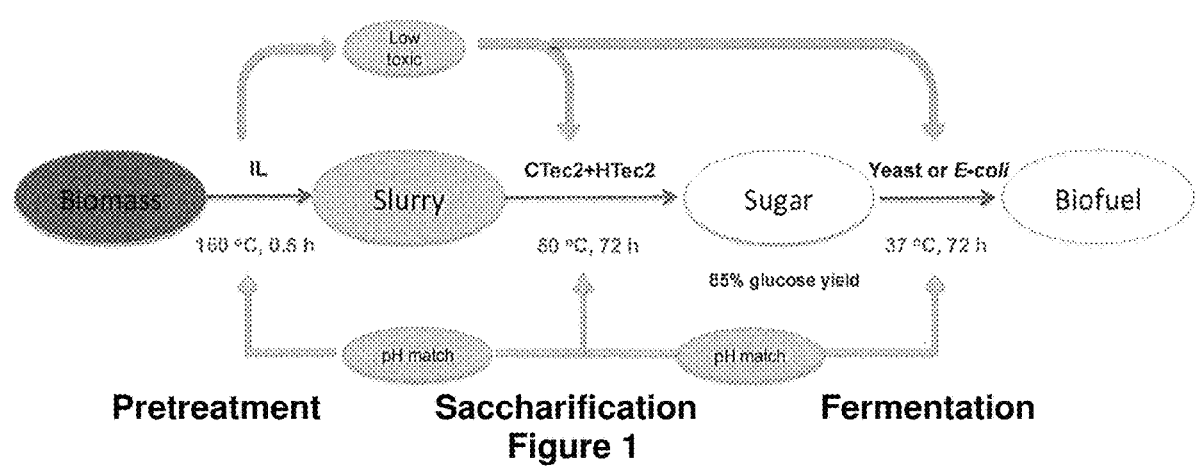

FIG. 1. One-pot process developed in this work.

Figure 2:
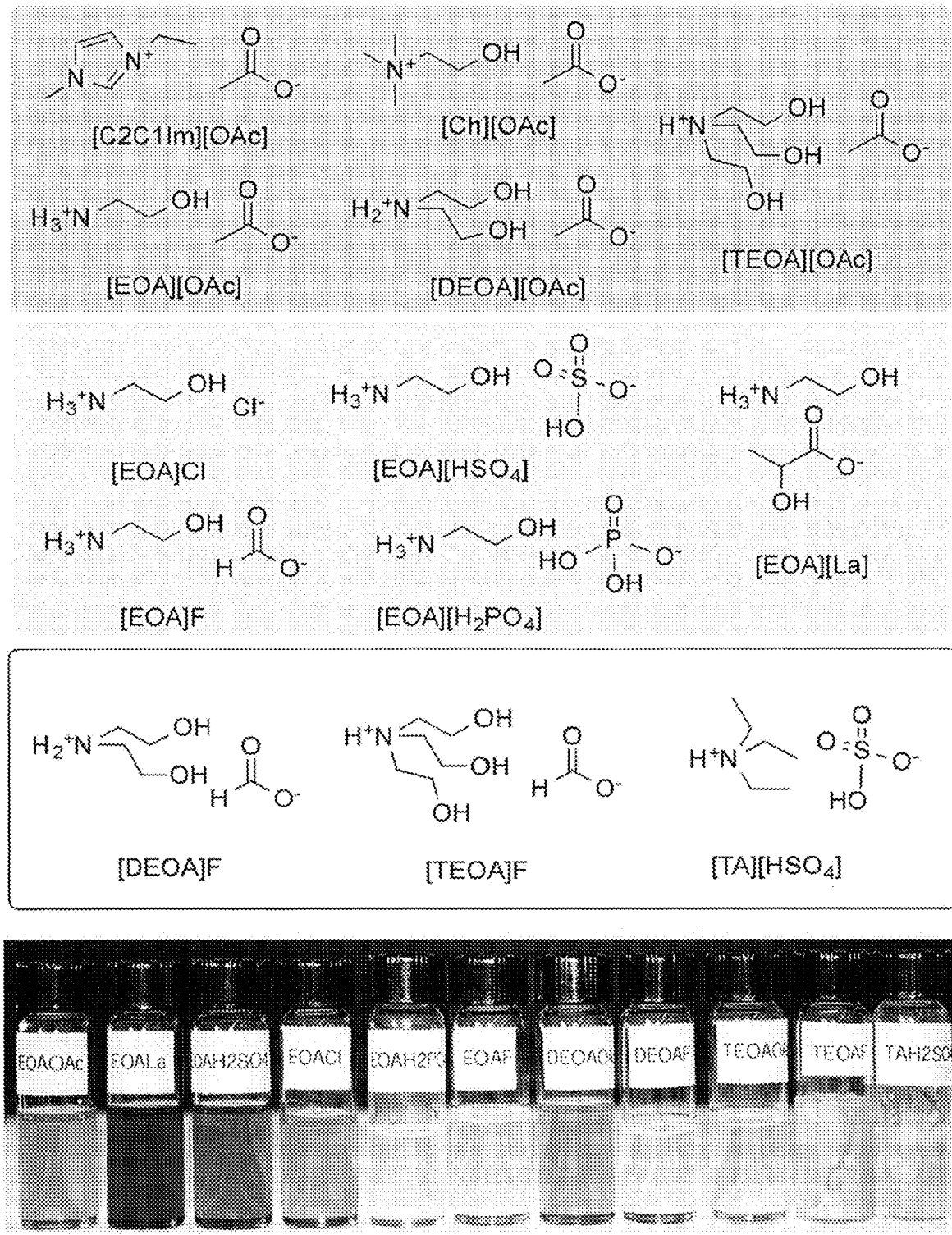

FIG. 2. The chemical structure of ILs employed in this work.

Figure 3:
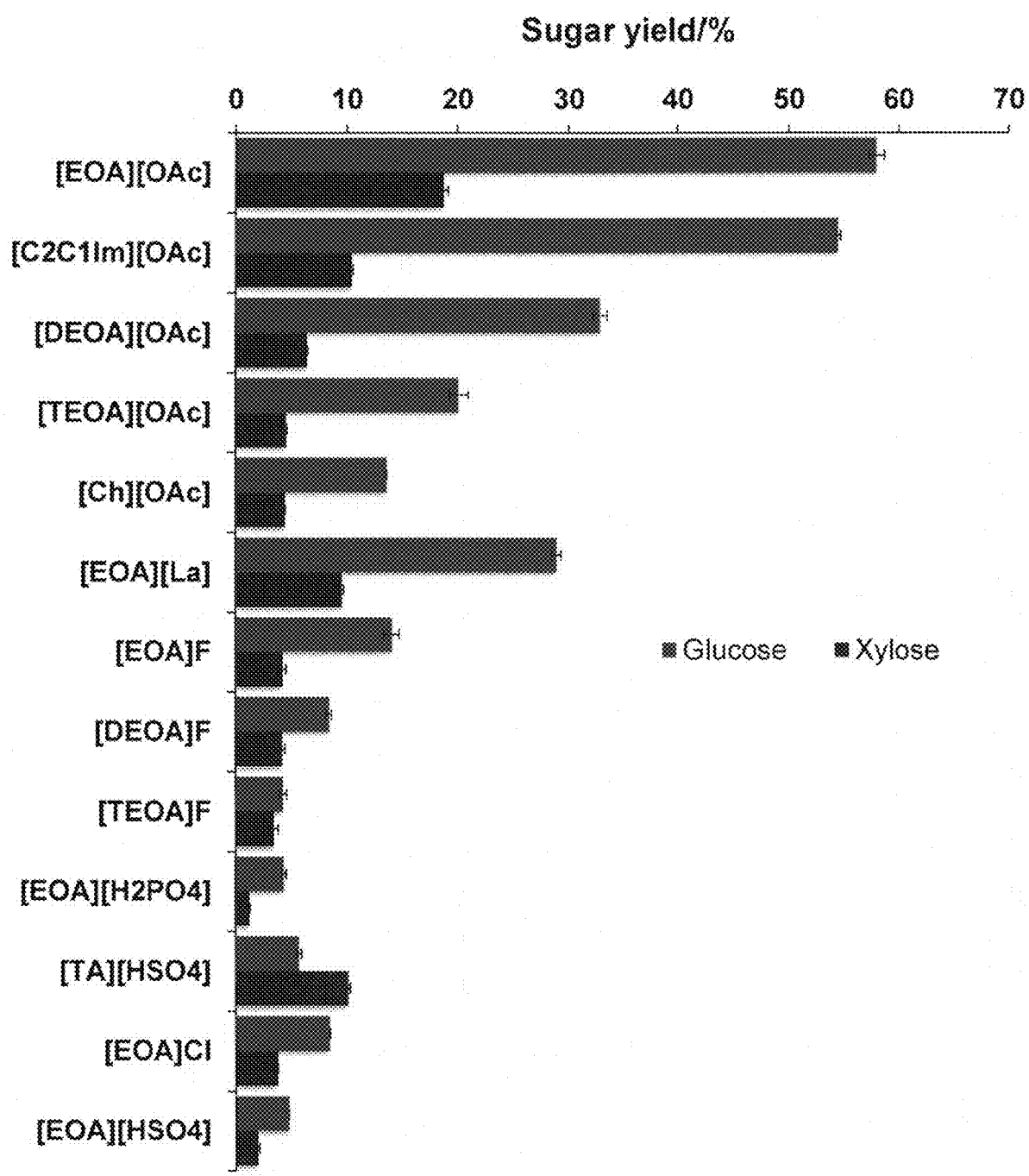

FIG. 3. Effect of IL type on the sugar yield (pretreatment: 10 wt % SG loading, 90 wt % IL, 140° C., 1 h, saccharification: 10 wt % IL, 10 mg protein per g switchgrass, 50 ° C., 72 h.

Figure 4A:
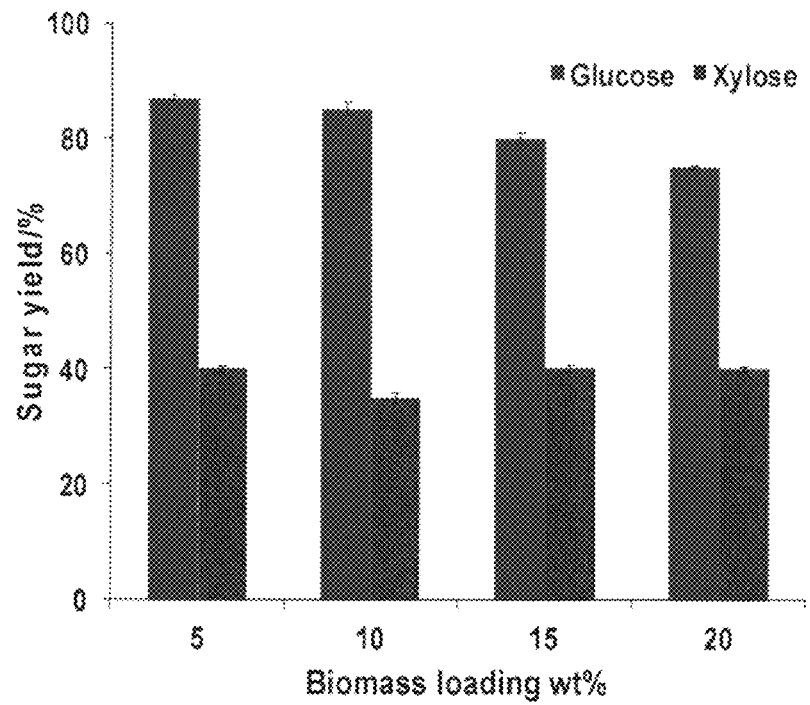

FIG. 4A. Effects of some parameters on the sugar yield: biomass loading at pretreatment. Normal operation conditions: pretreatment, 10 wt % SG loading, 90 wt % IL, 160° C., 0.5 h (3 h for eucalyptus); saccharification, 10 wt % IL, 20 mg protein/g SG, 50° C., 72 h.

Figure 4B:
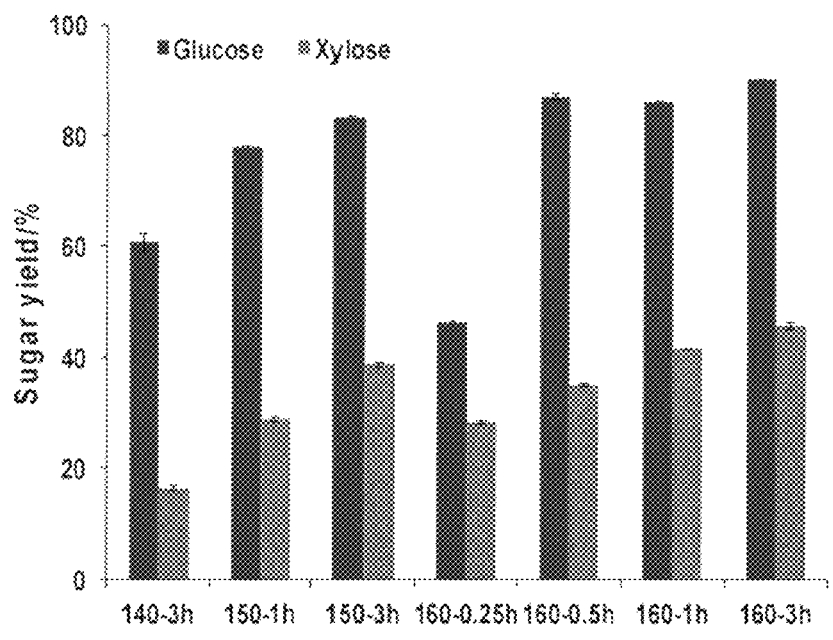

FIG. 4B. Effects of some parameters on the sugar yield: temperature/time. Normal operation conditions: pretreatment, 10 wt % SG loading, 90 wt % IL, 160° C., 0.5 h (3 h for eucalyptus); saccharification, 10 wt % IL, 20 mg protein/g SG, 50° C., 72 h.

Figure 4C:
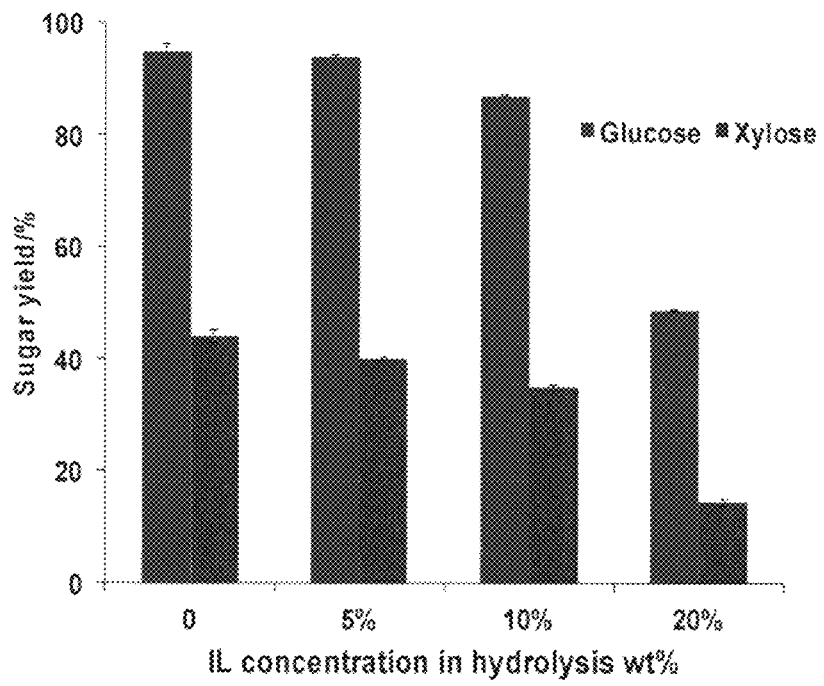

FIG. 4C. Effects of some parameters on the sugar yield: IL concentration in hydrolysis. Normal operation conditions: pretreatment, 10 wt % SG loading, 90 wt % IL, 160° C., 0.5 h (3 h for eucalyptus); saccharification, 10 wt % IL, 20 mg protein/g SG, 50 ° C., 72 h.

Figure 4D:
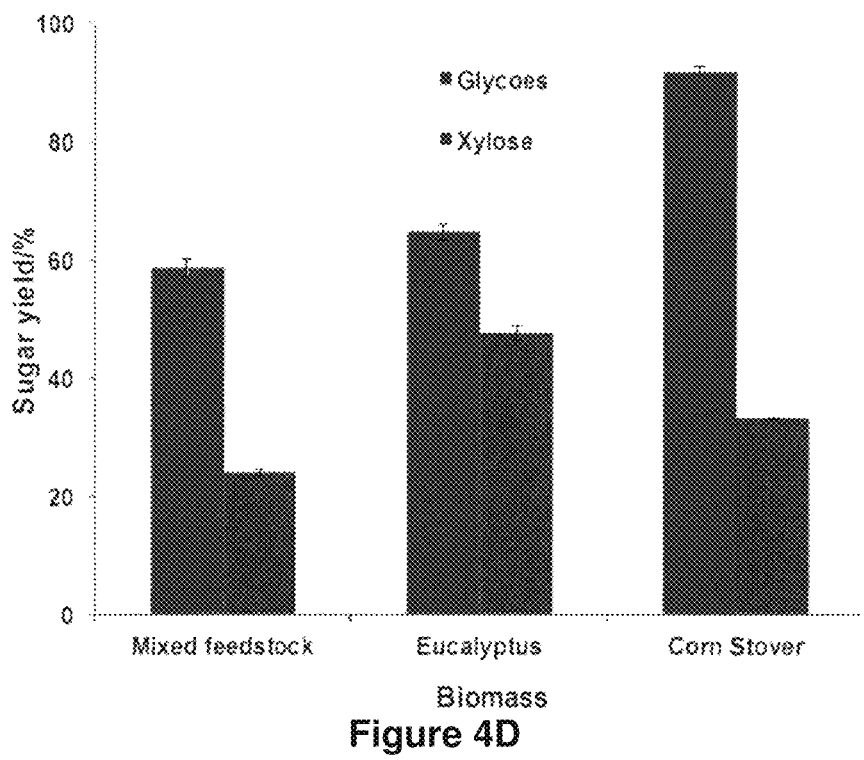

FIG. 4D. Effects of some parameters on the sugar yield: biomass category. Normal operation conditions: pretreatment, 10 wt % SG loading, 90 wt % IL, 160° C., 0.5 h (3 h for eucalyptus); saccharification, 10 wt % IL, 20 mg protein/g SG, 50° C., 72 h.

Figure 5A:
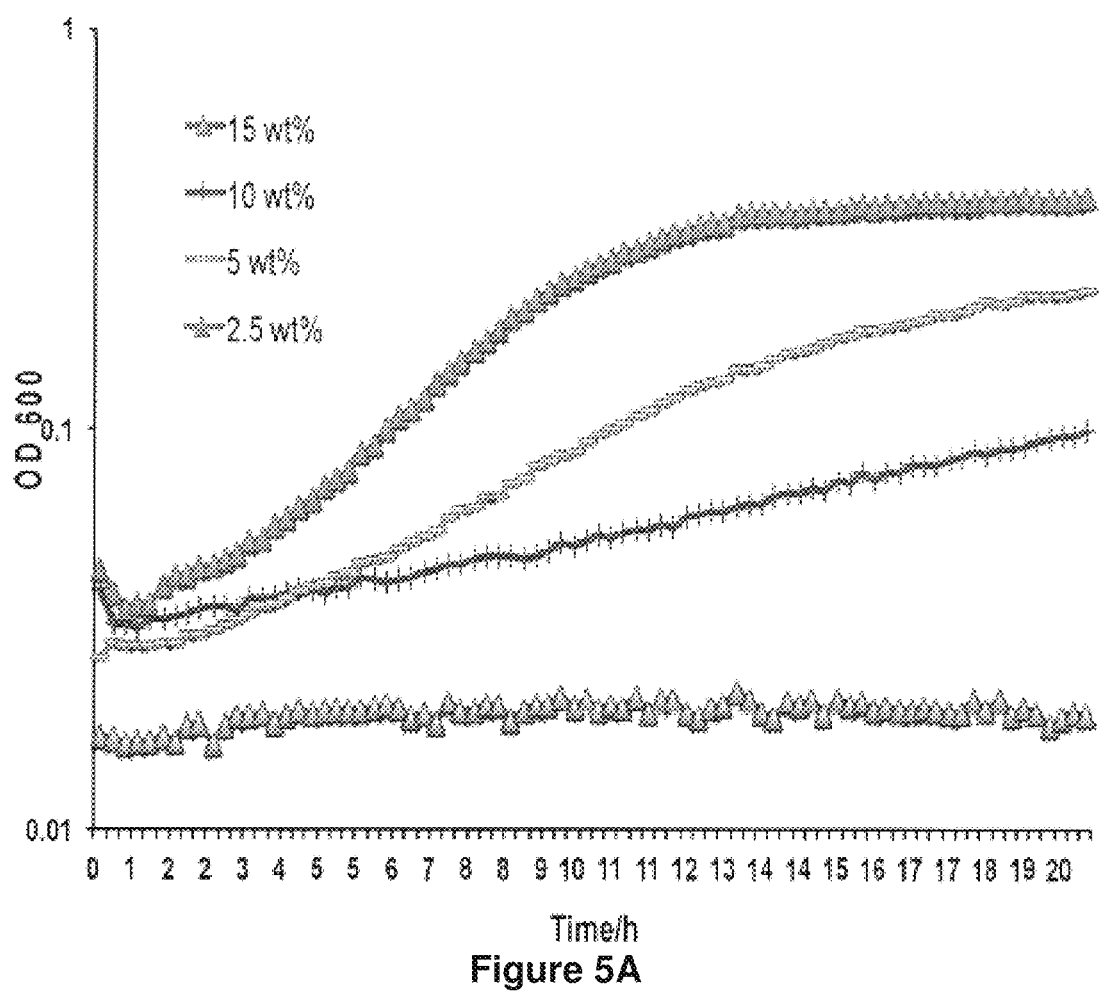

FIG. 5A. Toxicity test of [EOA][OAc]. Conditions: yeast strain: *Saccharomyces cerevisiae* strain BY4741, growth condition: in 24-well microplate with orbital-high intensity shaking/31° C./in IL solution (10 g/L glucose in each IL solutions), volume of the cell culture was 0.5 mL.

Figure 5B:
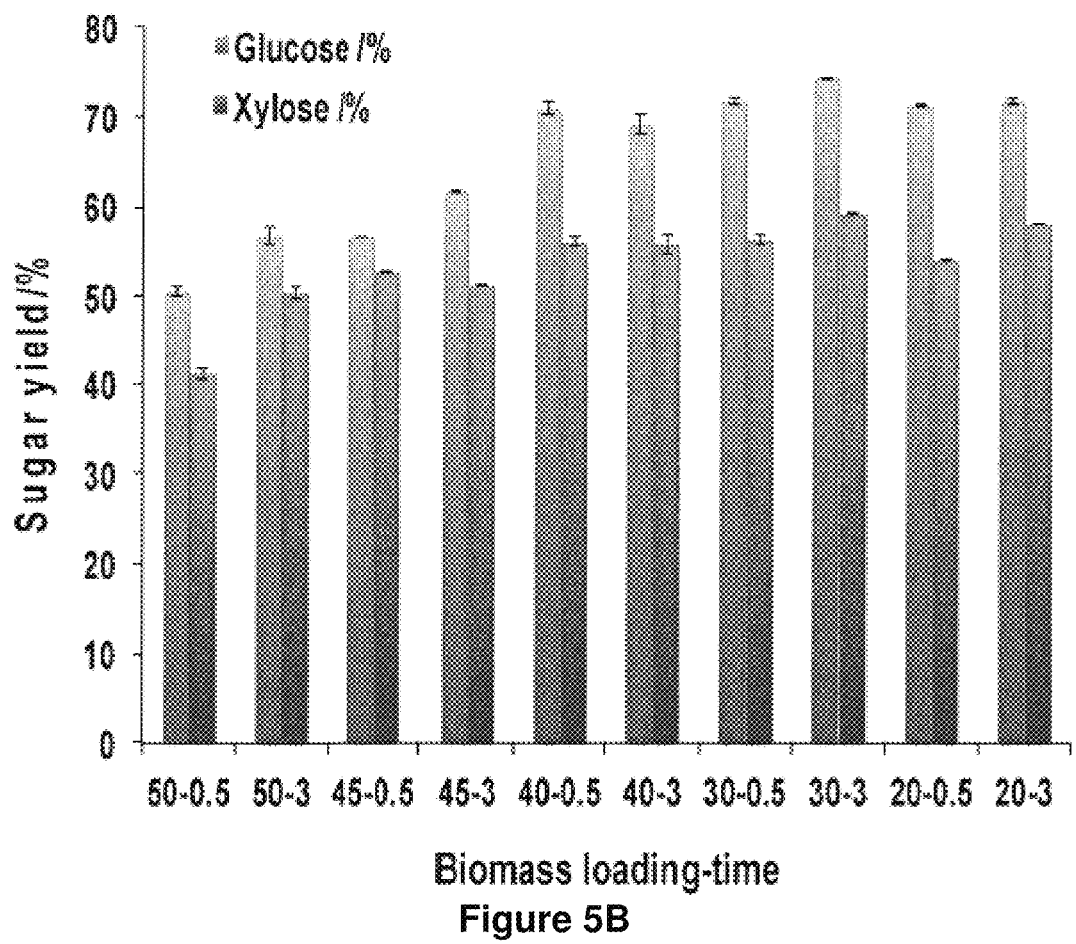

FIG. 5B. Effect of biomass loading on sugar yield. Conditions: pretreatment, x wt % SG loading, (100-x) wt % IL, 160° C., 0.5 h; saccharification, 5 wt % IL, 20 mg protein/g SG, 50° C., 72 h.

Figure 6A:
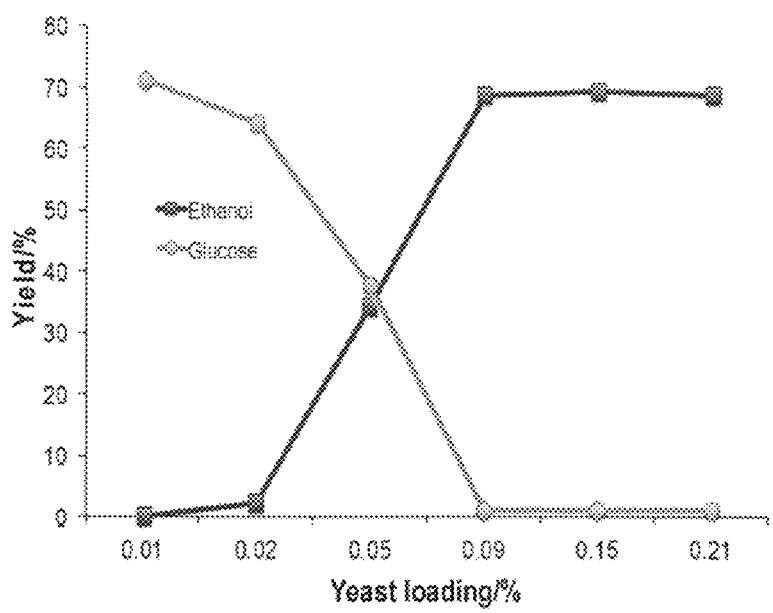

FIG. 6A. Process optimization of one-pot ethanol fermentation after [EOA][OAc] pretreatment. Effect of yeast loading on ethanol fermentation. Conditions: pretreatment, 40 wt % SG loading, 60 wt % IL, 160° C., 0.5 h; saccharification, 5 wt % IL, 20 mg protein/g SG, pH 5, 50° C., 24 h; fermentation, 37° C., 72 h.

Figure 6B:
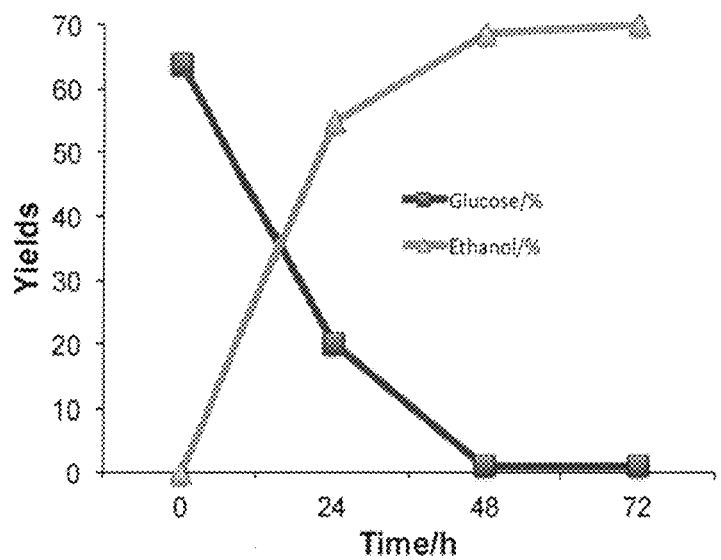

FIG. 6B. Process optimization of one-pot ethanol fermentation after [EOA] [OAc] pretreatment. Illustration of the glucose consumption and ethanol production during SSF. Conditions: pretreatment, 40 wt % SG loading, 60 wt % IL, 160° C., 0.5 h; saccharification, 5 wt % IL, 20 mg protein/g SG, pH 5, 50° C., 24 h; fermentation, 37° C., 72 h.

Figure 7:
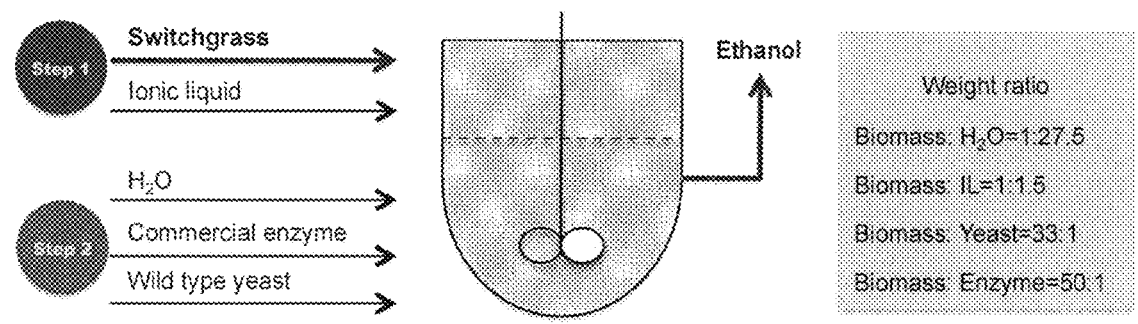
Figure 7:
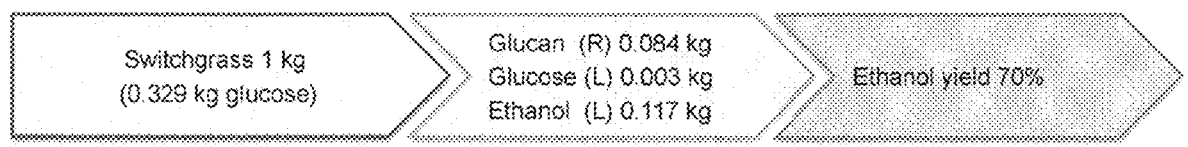

FIG. 7. Illustration of the glucose consumption and ethanol production during SSF. Conditions: pretreatment, 40 wt % SG loading, 60 wt % IL, 160° C., 0.5 h; saccharification, 5 wt % IL, 20 mg protein/g SG, 50° C., 24 h; fermentation, 37° C., 72 h.

Figure 8A:
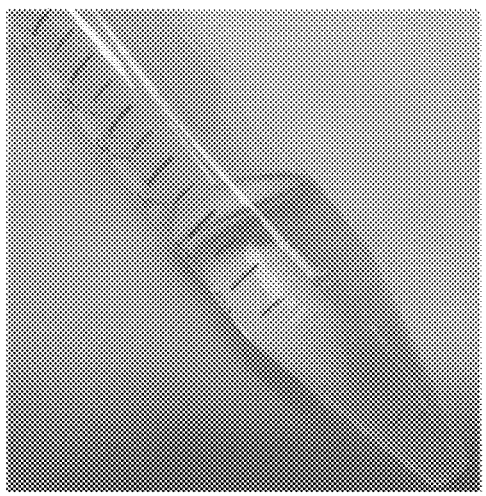

FIG. 8A. Dissolution, separation of lignin of ethylene glycol.

Figure 8B:
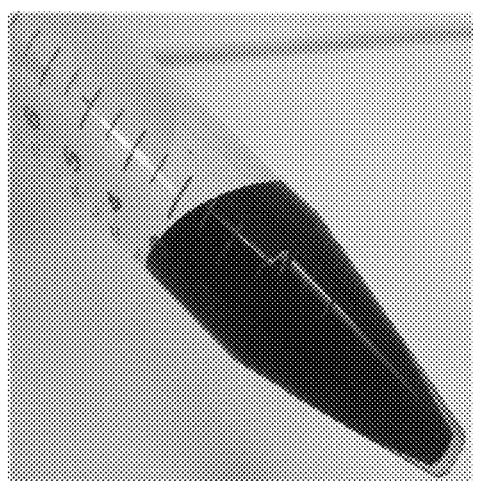

FIG. 8B. Dissolution, separation of lignin of ethylene glycol/lignin.

Figure 8C:
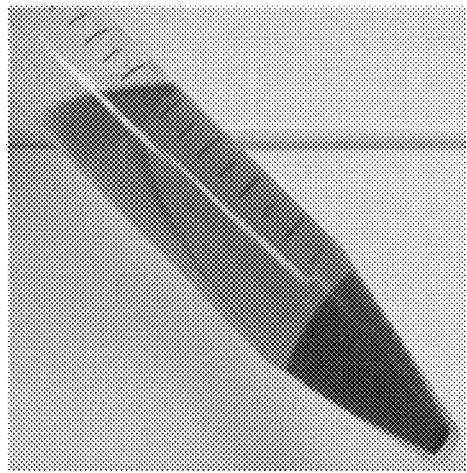

FIG. 8C. Dissolution, separation of lignin of ethylene glycol/lignin/ethanol.

Figure 8D:
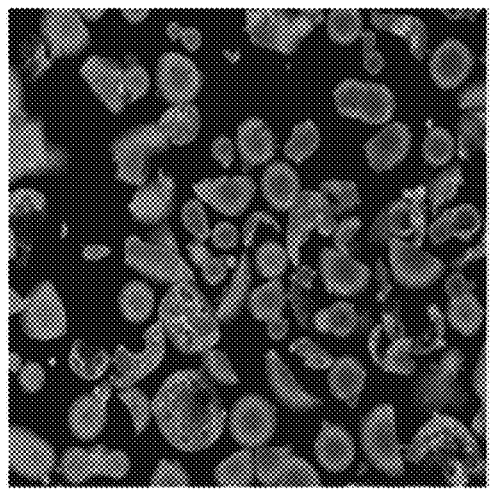

FIG. 8D. Fluorescence microscopy results (10×) for lignin dissolution in different solvents at room temperature for starting lignin.

Figure 8E:
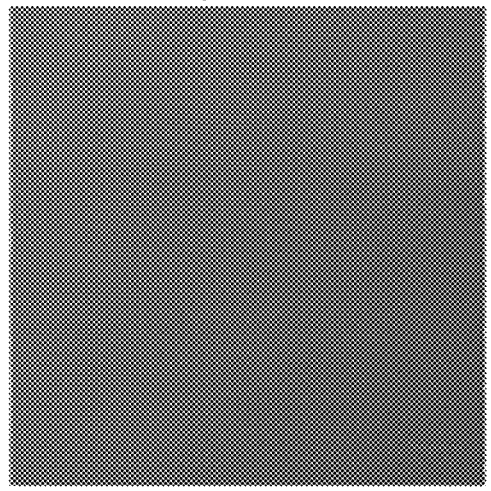

FIG. 8E. Fluorescence microscopy results (10×) for lignin dissolution in different solvents at room temperature for lignin/EG solution.

Figure 8F:
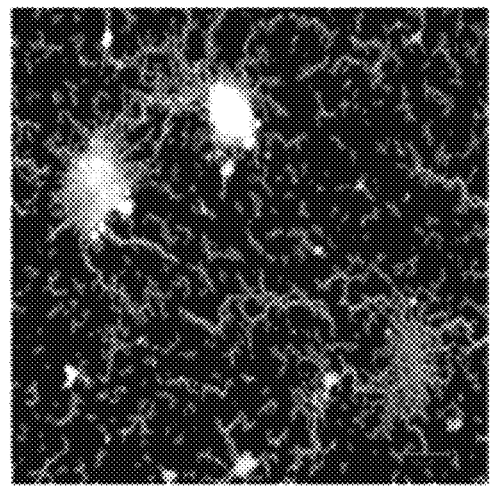

FIG. 8F. Fluorescence microscopy results (10×) for lignin dissolution in different solvents at room temperature for precipitated lignin.

Figure 9A:
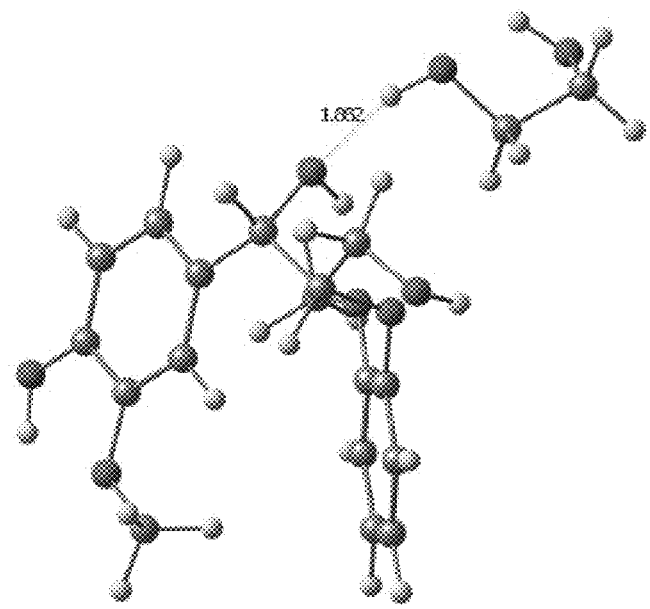

FIG. 9A. Optimized geometries of a dilignol-EG complex, Dilignol-EG$_1$ (α-C—OH), IE=8.39.

Figure 9B:
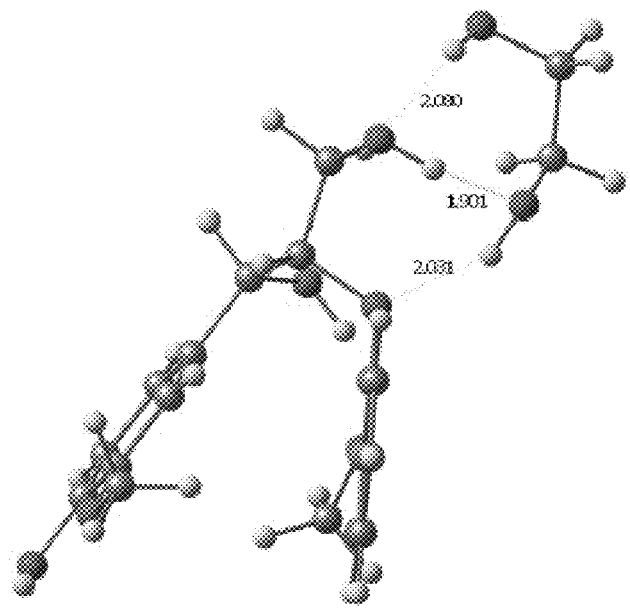

FIG. 9B. Optimized geometries of a dilignol-EG complex, Dilignol-EG$_1$ (γ-C—OH), IE=12.2.

Figure 9C:
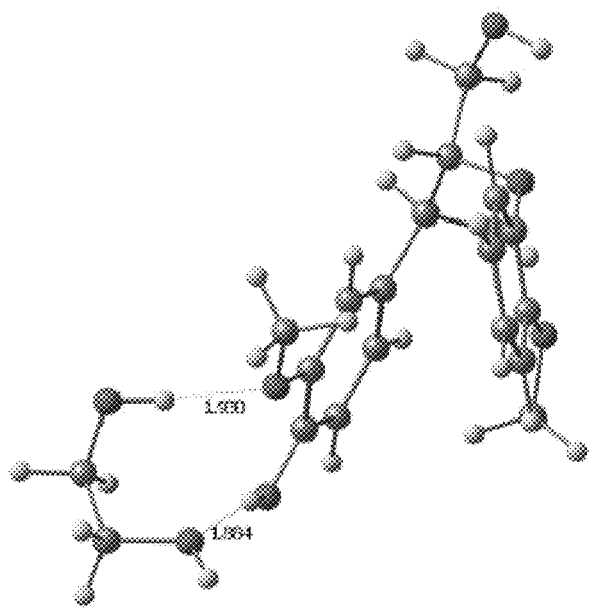

FIG. 9C. Optimized geometries of a dilignol-EG complex, Dilignol-EG$_1$ (ring-OH), IE=11.2.

Figure 9D:
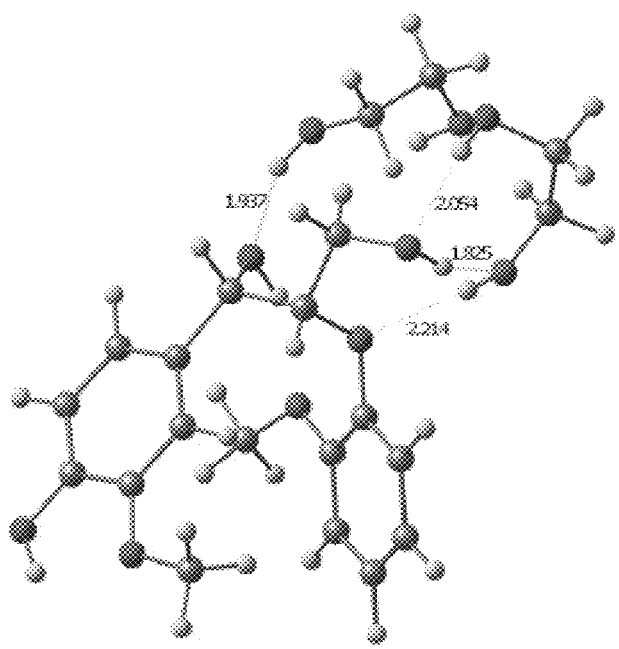

FIG. 9D. Optimized geometries of a dilignol-EG complex, Dilignol-EG$_2$, IE=22.9.

Figure 9E:
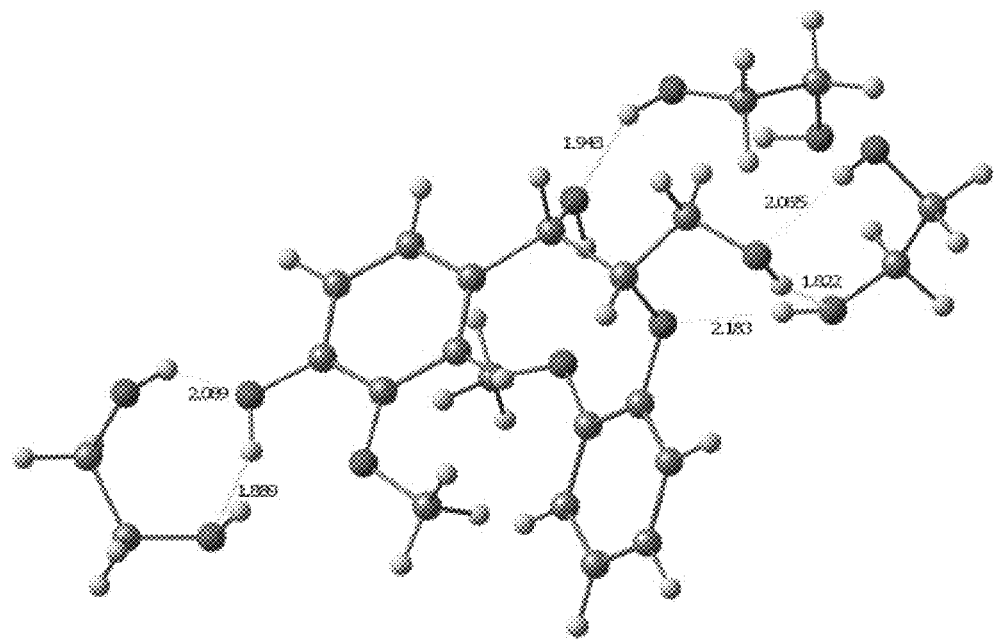

FIG. 9E. Optimized geometries of a dilignol-EG complex, Dilignol-EG$_3$, IE=33.8.

Figure 9F:
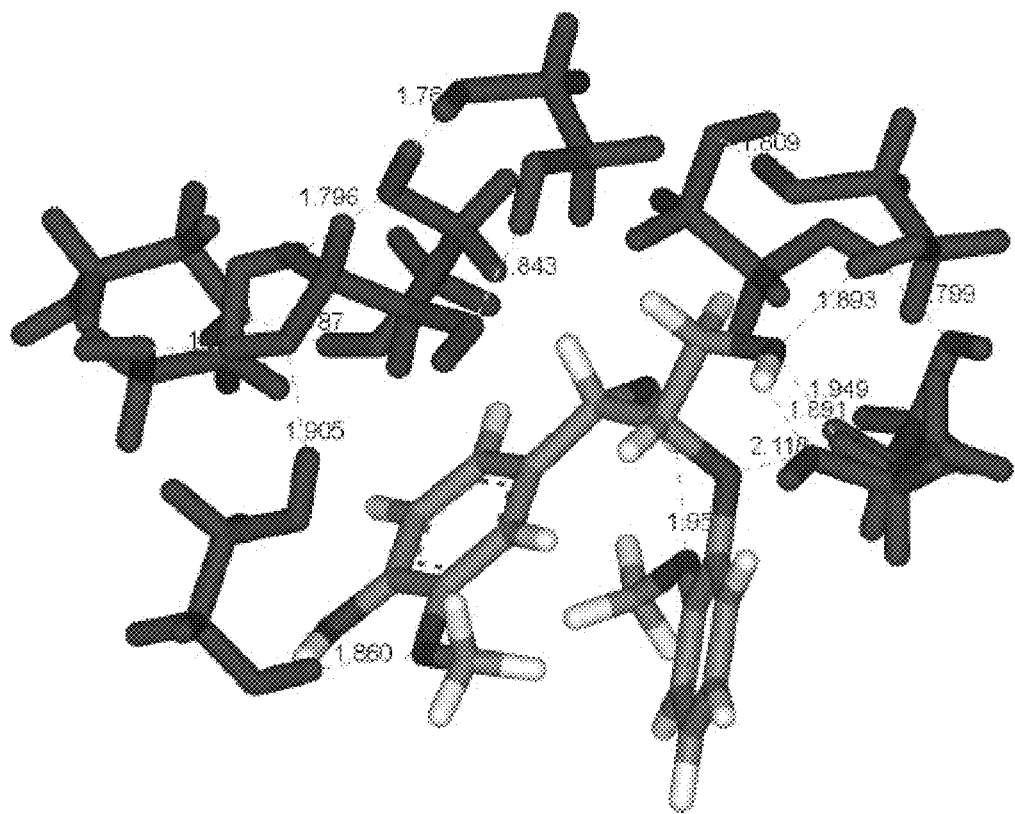

FIG. 9F. Optimized geometries of a dilignol-EG complex, Dilignol-EG$_{10}$ (EG shown in red), IE=133.4.

Figure 9G:
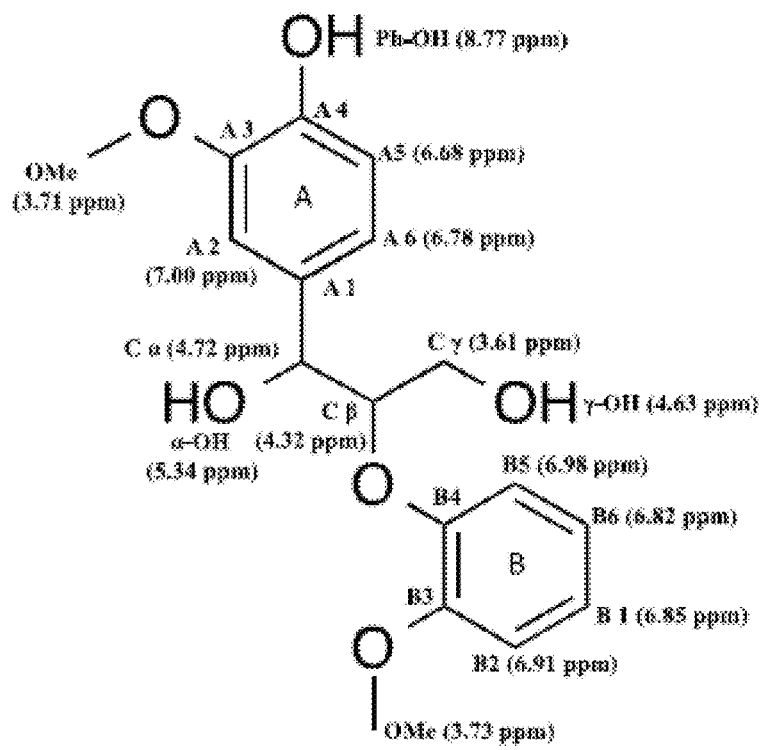

FIG. 9G. $^1$H NMR chemical shift assignment of dilignol in DMSO-d$_6$.

Figure 9H:
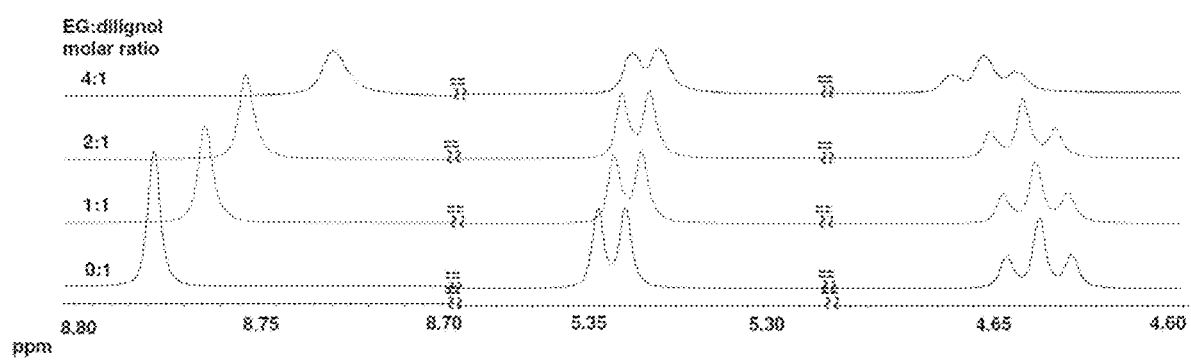

FIG. 9H. Effect of EG concentration on the 1H NMR chemical shifts of Ph-OH, α-C—OH, and γ-C—OH of dilignol. Only the Ph-OH and the hydroxyl protons are depicted. Interaction energy (IE) is reported in kcal/mol.

Figure 10:
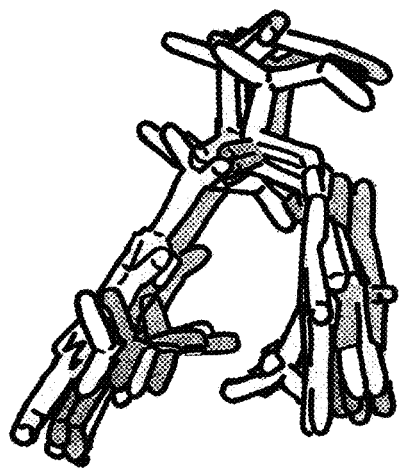

FIG. 10. Superimposed structures of the bare dilignol and isolated dilignol-EG$_1$, dilignol-EG$_3$, dilignol-EG$_1$-H$_2$O$_2$ and dilignol-EG$_{10}$ complexes.

Figure 11:
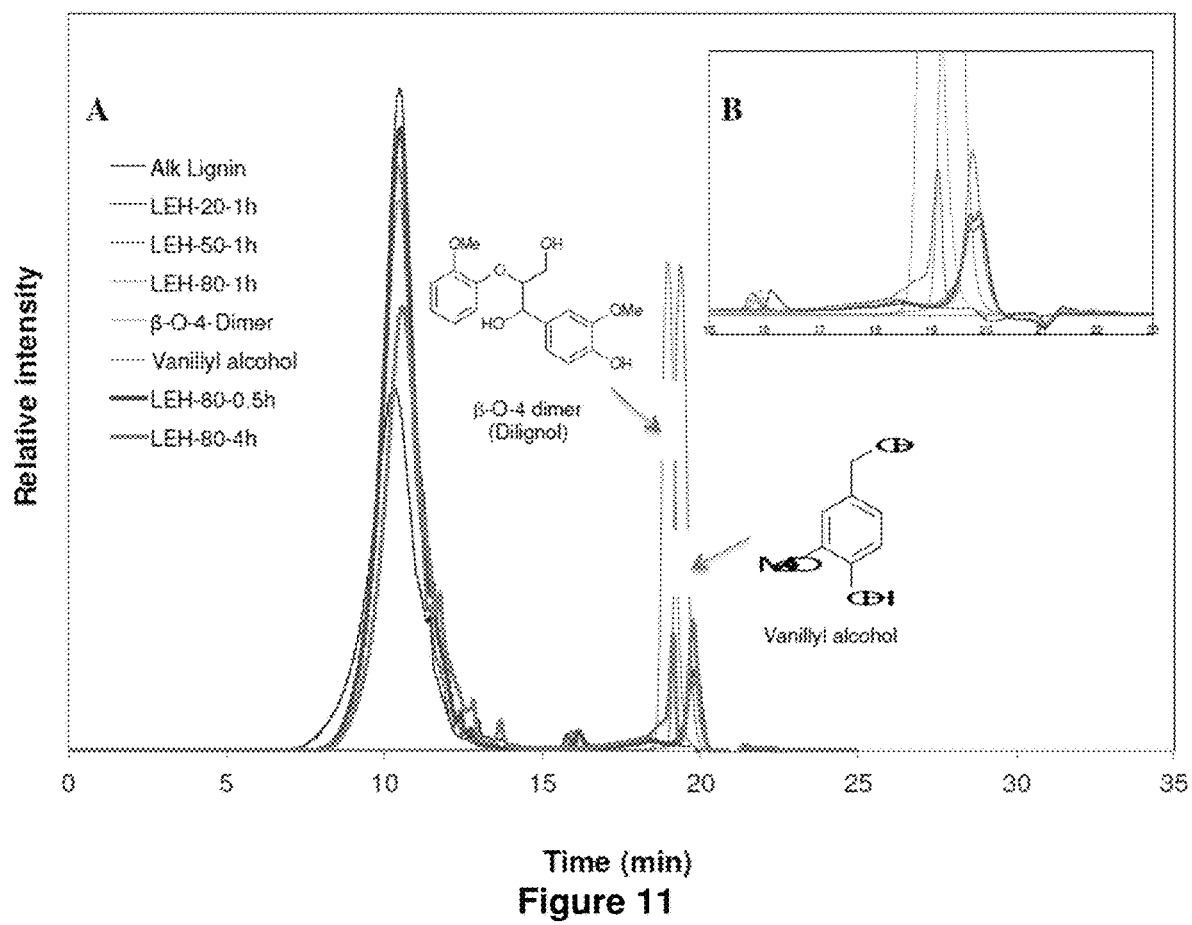

FIG. 11. Depolymerization of lignin in EG, H$_2$O and H$_2$O$_2$ system (A) and zoom in of low molecular range (B). Conditions: 10 wt % alkali lignin, 45 wt % EG, 45 wt % H$_2$O$_2$; LEH refers to lignin-ethylene glycol-hydrogen peroxide.

Figure 12A:
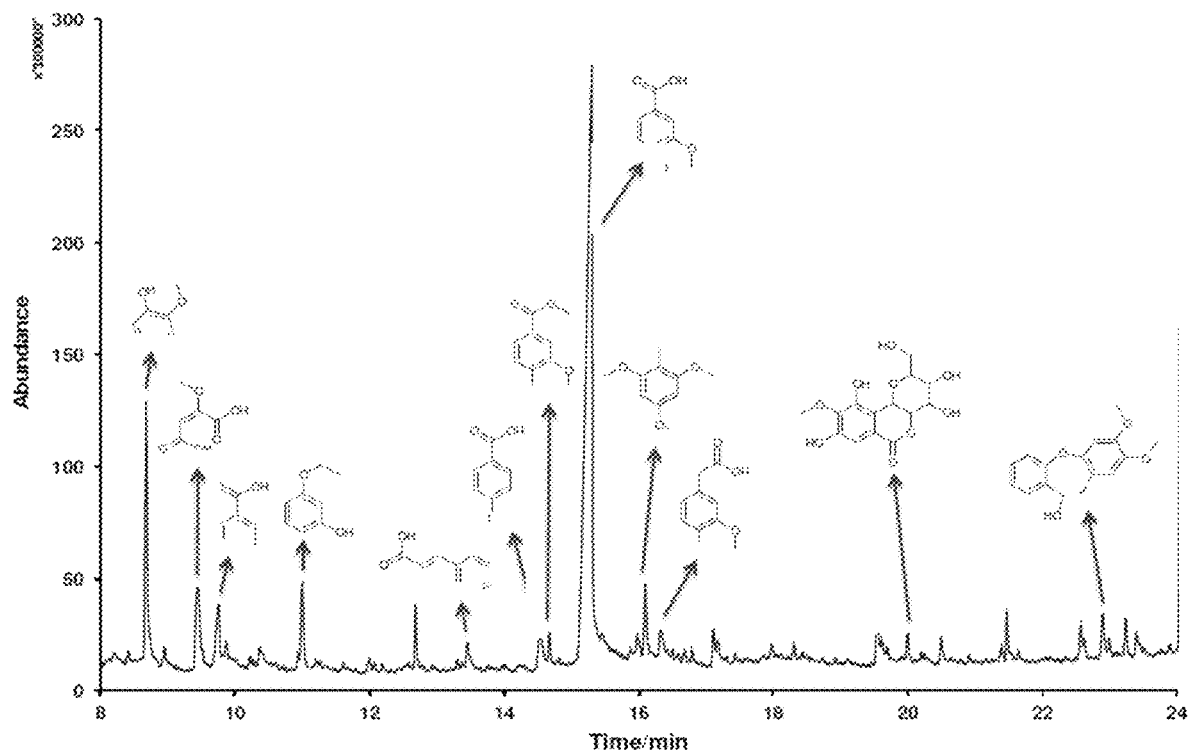

FIG. 12A. GC-MS spectrum of main depolymerized monomers of lignin. Conditions: 10 wt % lignin, 10 wt % EG, 80 wt % H$_2$O$_2$ (30 wt %), 80° C., 4 h.

Figure 12B:
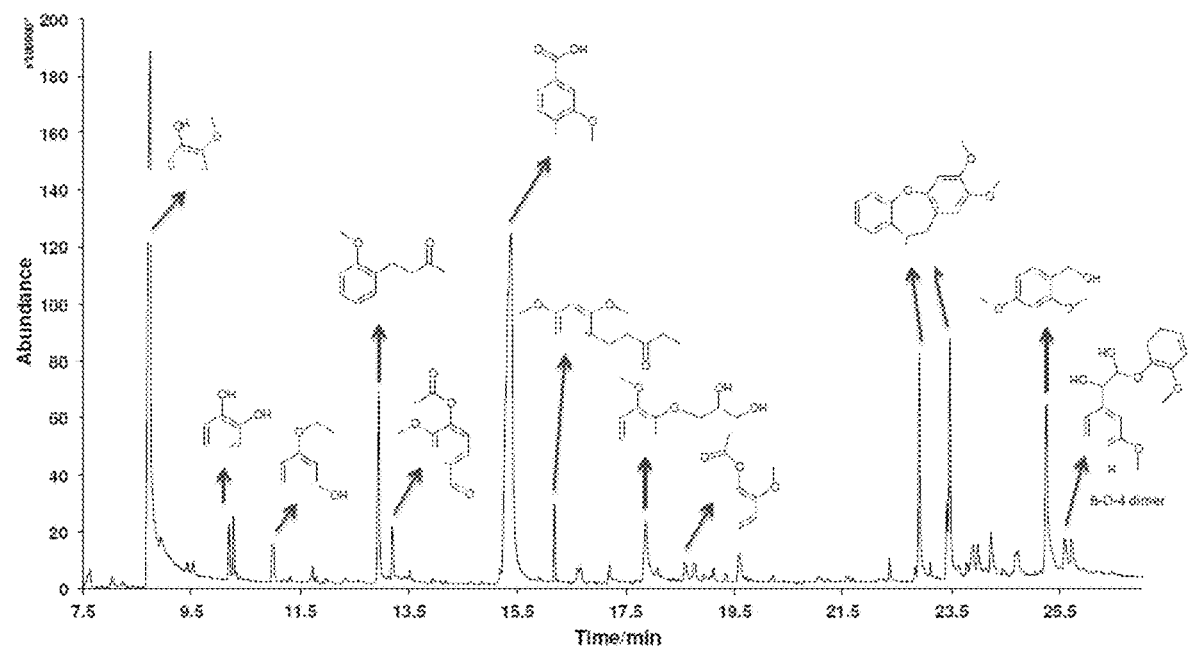

FIG. 12B. GC-MS spectrum of main depolymerized monomers of lignin. Conditions: 10 wt % dilignol (β-O-4 dimer model), 10 wt % EG, 80 wt % H$_2$O$_2$ (30 wt %), 80° C., 4 h.

DETAILED DESCRIPTION OF THE INVENTION

Before the invention is described in detail, it is to be understood that, unless otherwise indicated, this invention is not limited to particular sequences, expression vectors, enzymes, host microorganisms, or processes, as such may vary. It is also to be understood that the terminology used herein is for purposes of describing particular embodiments only, and is not intended to be limiting.

As used in the specification and the appended claims, the singular forms "a," "an," and "the" include plural referents unless the context clearly dictates otherwise. Thus, for example, reference to an "IL" includes a single IL compound as well as a plurality of IL compounds, either the same (e.g., the same molecule) or different.

In this specification and in the claims that follow, reference will be made to a number of terms that shall be defined to have the following meanings:

The terms "optional" or "optionally" as used herein mean that the subsequently described feature or structure may or may not be present, or that the subsequently described event or circumstance may or may not occur, and that the description includes instances where a particular feature or structure is present and instances where the feature or structure is absent, or instances where the event or circumstance occurs and instances where it does not.

The present invention provides for a method for dissolving and/or depolymerizing lignin comprising: (a) providing a composition comprising lignin, (b) contacting the composition with a strong hydrogen donor, such as a polyol, to form a first solution, (c) incubating the first solution at a temperature equal to or less than 100° C., whereby at least 20% by weight of the lignin is dissolved, (d) optionally introducing an oxidation agent to the first solution to form a second solution, wherein the temperature of the second solution is equal to or less than 100° C., whereby lignin is at least partly, substantially, or wholly depolymerized, and (e) optionally introducing an anti-solvent, such as an alcohol, such as ethanol or isopropanol, to the second solution to precipitate the depolymerized lignin.

In some embodiments, the composition is a biomass comprising lignin. In some embodiments, the composition is a biomass further comprises a cellulose, hemicellulose, and/or polysaccharide, and the method further comprises adding a cellulase to the second solution whereby the polysaccharide is cellulose, hemicellulose, and/or polysaccharide is at least partly, substantially, or wholly depolymerized.

In some embodiments, the composition of step (a) comprises a high solid loading whereby the composition comprises equal to or more than 10%, 20%, 30%, 40%, or 50% by weight of a solid comprising the lignin, such as a biomass comprising the lignin.

In some embodiments, the polyol is an alkyl polyol. In some embodiments, the alkyl polyol has an alkyl chain of 10 or fewer, 9 or fewer, 8 or fewer, 7 or fewer, 6 or fewer, 5 or fewer, 4 or fewer, 3 or fewer, or 2 or fewer carbon atoms. In some embodiments, the alkyl polyol is ethylene glycol (EG), propylene glycol, or glycerin (glycerol). In some embodiments, the first solution and/or second solution has, or is incubated at, a temperature of equal to or less than 90° C., 80° C., 70° C., 60° C., 50° C., 40 ° C., 30° C., or 20° C., or a temperature having a value within any two of the preceding expressed temperatures. In some embodiments, step (c) results in the dissolution of at least 25%, 30%, 35%, 40%, 45%, or 50% by weight of the lignin.

In some embodiments, the oxidation agent is hydrogen peroxide, HNO$_3$, Br$_2$, IO$_3^-$, CrO$_4^-$, Pt$^{2+}$, MnO$_2$, O$_2$, Cr$_2$O$_7^{2-}$, Cl$_2$ (g), PbO$_2$, MnO$_{4-}$, Co$^{3+}$, S$_2$O$_8^{2-}$, O$_3$ (g), or F$_2$ (g). In some embodiments, the oxidation agent is any agent that is a stronger oxidizing agent than hydrogen peroxide. In some embodiments, step (d) the depolymerization of lignin results in the formation of one or more, or a mixture of the depolymerized lignin compounds shown in FIGS. 12A and 12B. In some embodiments, the depolymerized lignin compound has two or fewer, one or fewer, or no benzene ring.

The present invention provides for a composition and methods for depolymerizing lignin as described herein. The present invention provides a process in which higher loading lignin is dissolved at a lower temperature, and/or the dissolved lignin is depolymerized into lower molecular weight at a temperature as low as possible. In some embodiments, the above two processes are performed separately or coupled together at room temperature.

The present invention provides for a mild route to dissolve and depolymerize lignin under low temperature. The advantages of this method are listed below:

(a) In some embodiments, the method is capable of dissolving lignin with more than 30 wt % in solvent (such as, ethylene glycol, propylene glycol, glycerin, and the like) under a low temperature, such as below 100° C. (e.g., room temperature). After dissolution, adding anti-solvent (such as, ethanol, isopropanol, and the like), lignin can be precipitated efficiently from the system, and the solvent can be easily recycled and reused.

(b) In some embodiments, the dissolution process only requires cheap and environmental benign chemicals and relatively simple reaction conditions.

(c) In some embodiments, the method is capable of depolymerization of lignin in the presence of carbonic acid and/or hydrogen peroxide. The carbonic acid was formed in-situ utilizing carbon dioxide and water at a certain pressure condition.

(d) In some embodiments, the depolymerization process can be operated at low temperature (such as, below 100° C.) and even at room temperature.

(e) In some embodiments, the method can be used in conjugation with ionic liquids for tailoring the solvation and chemical properties of the process, the ILs used could be found such as [C2C1 Im][OAc], [C4C1 Im]Cl and choline chloride, etc.

(f) In some embodiments, the method can be extended to real biomass for biofuel applications.

This invention represents a new route to efficiently dissolve and depolymerize lignin under mild conditions that could significantly improve the economics of a biorefinery.

Formation of strong hydrogen bonding interaction between solvent (e.g. ethylene glycol) and lignin molecules might be the reason for the higher solubility of lignin at lower temperature. On the other hand, proton from in-situ generated carbonic acid results in low temperature depolymerization of lignin. Also, the presence of hydrogen peroxide plays an oxidation role in producing dimer/monomer lignin products. This invention provides a method by combining hydrogen bond and proton donors for low temperature processing and depolymerization of lignin.

The present invention also provides for a method of pretreating biomass comprising contacting a biomass with a low toxic inexpensive protic ionic liquid (PIL) to form a solution, and optionally saccharifying or simultaneous saccharifying and fermenting the solution in the presence of an enzyme, such as a cellulase.

The PIL comprises a cheap ion derived from a simple amino base, such as ethanolamine, diethanolamine, or triethanolamine choline, and a common commercially available acid, such as acetic acid, sulfuric acid, phosphoric acid, hydrochloric acid, and formic acid. In some embodiments, the method does not comprise any pH adjustment, water-washing step.

It is to be understood that, while the invention has been described in conjunction with the preferred specific embodiments thereof, the foregoing description is intended to illustrate and not limit the scope of the invention. Other aspects, advantages, and modifications within the scope of the invention will be apparent to those skilled in the art to which the invention pertains.

All patents, patent applications, and publications mentioned herein are hereby incorporated by reference in their entireties.

The invention having been described, the following examples are offered to illustrate the subject invention by way of illustration, not by way of limitation.

EXAMPLE 1

One-pot Integrated Cellulosic Ethanol Production Enabled by Inexpensive Protic Ionic Liquids Practically useful ionic liquids (ILs), such as 1-ethyl-3-methylimi-dazolium acetate ($[C_2C_1Im][OAc]$), and choline lysinate ([Ch][Lys]) are highly effective for the pretreatment of lignocellulosic biomass. However, employing ILs like those in one-pot bioproces sing from biomass to biofuel still remains challenges such as toxicity, water-washing requirement or pH compatibility problems. To address these issues, herein, for the first time, we demonstrated one-pot integrated cellulosic ethanol production enabled by low toxic inexpensive protic ILs (PILs) under water-washing free and pH adjustment free conditions. These PILs are consisting of cheap ions derived from simple amino bases (e.g., ethanolamine, diethanolamine, or triethanolamine, choline) and acids from common commercial sources (e.g., acetic acid, sulfuric acid, phosphoric acid, hydrochloric acid and formic acid). Without pH adjustment and water-washing operation the pretreatment slurry could be directly used for saccharification and simultaneous saccharification and fermentation (SSF) in the presence of commercial enzyme and/or wide type yeast. As two options, 85% glucose and 35% xylose (monomers) could be liberated from switchgrass (SG), and a 70% of theoretical ethanol yield could be obtained in SSF by using as high as 40% SG loading at pretreatment step. This study opens avenues for improvement of efficiency and lowering of cost IL pretreatment process.

Introduction

As well known, an exhausted situation of fossil energy has stimulated the interest and requirement in exploring new renewable energy resources. In this context, lignocellulosic biomass is a promising feedstock for commercial scale production of fuels and bio-commodities due to its high abundance and geographic availability.[1] However, before they can be efficiently transformed by enzymatic saccharification to fermentable sugars, the crystallinity of cellulose, accessible surface area, protection of cellulose by lignin, the heterogeneous character of biomass particles, and cellulose sheathing by hemicellulose all contribute to the recalcitrance of lignocellulose to hydrolysis.[2] Up till now, several physical and/or chemical pretreatment approaches have been investigated over the past decades including popular protocols such as dilute acid/base, hot water, and steam explosion pretreatment.[1] Among these techniques, ionic liquids (ILs) have shown some very promising aspects as a pretreatment media for biomass due to their unique physicochemical properties, such as low vapor pressure, high thermal stability, wide liquid range, designability and high solvation ability to dissolve various organic and inorganic substance.[3] Using certain ILs, such as 1-ethyl-3-methylimidazolium acetate ($[C_2C_1Im]$ [OAc]), a IL pretreatment process can pretreat both single feedstock or a mixture of feedstock, including softwood and hardwood, at high solid loadings[4] and recently has been tested to liters scale,[5] and in continuous mode.[6] Thus, there has been an upsurge of interest in the use of ionic liquid for the pretreatment.

However, some challenges on IL based pretreatment process highly need to be concerned. The first one is that how to avoid the removal of residual amounts of ILs in biomass post-pretreatment. This excessive use of water and waste disposal associated with washing poses a challenge for the scale-up of any IL pretreatment technology.[7] The second challenge is the pH compatibility problem especially in a case of basic IL based pretreatment process. In our previous work, it has been proved that basic ILs such as 1-ethyl-3-methylimidazolium lysinate, 1-ethyl-3-methyl-imidazolium acetate, cholinium lysinate, and cholinium acetate, exhibit high pretreatment performance due to their high lignin removal ability,[8] and thus have been widely investigated. In this context, there is a series conflict of pH condition between pretreatment and enzymatic saccharification, which is a problem with the basic ILs. To resolve this problem, IL removal by water or pH adjustment by mineral acid is often used, which also result in a difficult separation of ILs or an invalid IL. The third challenge is the using of commercial enzyme cocktails. Despite the high effectiveness of using 1-ethyl-3-methylimidazolium acetate ([$C_2C_1$Im][OAc]) at reducing the recalcitrance of lignocellulosic biomass to enzymatic degradation, the low biocompatibility of imidazolium based ILs poses strong inhibitory effects to cellulases and fuel fermenting microbes. As a result, high cost IL tolerance enzyme (i.e. J Therm),[7] or IL removal after pretreatment is also needed. Based on the above discussions, development of biocompatible IL based washing-free pretreatment process with commercial enzyme is still highly required.

Recently, investigations on the application of hydroxyl ammonium ILs have been widely carried out. Compared to imidazolium categories ILs, these class of ILs are intrinsically less expensive, more easily synthesized, higher biodegradable and better biocompatible.[9,10,11,12,13] They have found various applications in biomass pretreatment,[8] $CO_2$ absorption/separation/conversion[11,14,15,16] $SO_2$ capture/gas desulfurization,[17,18,19] and anti-microbial.[20] In this paper, we have developed a process in which a cheap pH matched IL was used instead of traditional imidazolium based IL. The ILs contained ions derived from simple amino bases (e.g., ethanolamine, diethanolamine, or triethanolamine choline) and acids (e.g., acetic acid, sulfuric acid, phosphoric acid, hydrochloric acid and formic acid). The developed ILs could pretreat biomass efficiently, thereafter without pH adjustment and washing operation the resulted system could be used directly for the enzyme saccharification process in the presence of commercial enzyme cocktails. As a result, 85% glucose and 35% xylose (monomers) could be liberated from switchgrass. The use of pH matched IL for the one-pot pretreatment and saccharification of biomass represents a novel route that: 1) Using cheap, simple and efficient ILs for the one-pot process; 2) Enables one-pot IL biomass pretreatment and saccharification processes that does not require special IL tolerant enzyme cocktails, or extensive wash in traditional 2 step IL pretreatment and hydrolysis operations; 3) Doesn't require addition of mineral acids/organic acids to adjust pH since the pH of IL is matched with commercial enzyme cocktails.

Results and Discussion

Screening of ILs

The protic ionic liquids (PILs) are prepared through the stoichiometric neutralization reaction of certain Brønsted acids and Brønsted bases. The cations of the investigated PILs shown in FIG. 2 were chosen from simple and inexpensive compounds such as ethanolamine (EOA), diethanolamine (DEOA), triethanolamine (TEOA), and triethylamine (TEA), while the encountered anions were derived from normal organic and mineral acids such as acetic acid, lactic acid, sulfuric acid, phosphoric acid, formic acid and hydrochloric acid. For comparisons, choline acetate ([Ch][OAc]) and 1-ethyl-3-methyl imidazolium acetate ([$C_2C_1$Im][OAc]) were also investigated.

Continued search for an IL with the desirable physical, chemical and biological properties for biomass pretreatment is not viable without the aid of fundamental understanding and predictive development. Solubility is critical property for effective biomass pretreatment for higher sugar yield, either one of the major biomass compounds such as cellulose, lignin, and hemicelluloses needs to be preferentially dissolved by solvents. The inherent intricacy of these biomass compounds associated to the many different types of possible interactions allows very selective dissolution in wide range of different ILs. It has been shown that solvent parameters such as basicity ($\beta$) correlates well with an IL's ability to dissolve lignocellulose,[21,22] and that net basicity correlates with an IL's ability to dissolve cellulose.[22,23]

It has been demonstrated that the ILs computed net basicity value correlates with the ability of the ILs to efficiently pretreatment biomass. We calculated molecular acidity, basicity, and net basicity values as well as optimized geometries for these synthesized PILs using a set of DFT based global descriptors such as chemical potential ($\mu$) and chemical hardness ($\eta$) from the standard working equations. Table 1 shows IL solvent parameters for ILs investigated here. Comparison of the experimental results with the calculations of solvent parameters of these ILs shows that effective pretreatment requires an IL with high net basicity. Notably, ethanolamine acetate ([EOA][OAc]) IL has highest net $\beta$ values as compared with the other ILs selected in this investigation for screening. The net basicity values of PILs are considerably higher than [$C_2C_1$Im][OAc] and [Ch][OAc] except ethanolamine chloride ([EOA]Cl), ethanolamine bisulfate ([EOA][$HSO_4$]) and ethylamine bisulfate ([EA][$HSO_4$]). Predictably, more acidic anion counterpart lowering the net basicity values of ILs and an increase in ethyl groups of cations are gradually decreeing the ILs net basicity. From Table 1, it also can be seen that net basicity of ILs [EOA][OAc], diethanolamine acetate ([DEOA][OAc]), ethanolamine formate ([EOA]F) and ethanolamine dihydrogen phosphate ([EOA][$H_2PO_4$]) are higher than that of [$C_2C_1$Im][OAc]. In comparison with [Ch][OAc], —$NH_3^+$ group in [EOA] framework tends to have strong hydrogen bonding interactions between hydroxyl groups of lignocellulosic components; hence these ILs could enhance biomass solvation. Besides, the key properties that distinguish PILs from other ILs are the reversible proton transfer from the base to acid, by which the organic base could be generated as an efficient lignin removal solvent for biomass pretreatment.

TABLE 1

Calculated basicity ($\beta$), acidity ($\alpha$), and net basicity values of protic ILs.

| | $\beta$ | $\alpha$ | Net Basicity |
|---|---|---|---|
| [EOA][OAc] | 4.17 | 2.47 | 1.7 |
| [DEOA][OAc] | 4.08 | 2.44 | 1.64 |
| [TEOA][OAc] | 3.64 | 2.73 | 0.91 |
| [EOA]Cl | 3.21 | 2.7 | 0.52 |
| [EOA][$HSO_4$] | 3.56 | 3.1 | 0.46 |
| [EOA][$H_2PO_4$] | 4.17 | 2.63 | 1.55 |
| [EOA][La] | 4.04 | 2.84 | 1.2 |
| [EOA]F | 4.18 | 2.55 | 1.63 |

TABLE 1-continued

Calculated basicity (β), acidity (α), and net basicity values of protic ILs.

| | β | α | Net Basicity |
|---|---|---|---|
| [DEOA]F | 4.05 | 2.48 | 1.57 |
| [TEOA]F | 3.68 | 2.82 | 0.86 |
| [TA][HSO$_4$] | 3.63 | 2.68 | 0.95 |
| [C$_2$C$_1$Im][OAc] | 2.97 | 2.28 | 0.69 |
| [Ch][OAc] | 2.82 | 2.53 | 0.29 |
| [EA][H$_2$PO$_4$] | 4.35 | 2.79 | 1.56 |
| [EA][OAc] | 4.2 | 2.68 | 1.52 |
| [EA][HSO$_4$] | 3.52 | 3.01 | 0.51 |

To verify the simulation results, the investigation on the effect of PILs on the sugar yield was carried out under low pretreatment temperature and enzyme loading. Among all the PILs, [EOA] [OAc] was the best efficient IL for achieving high sugar yield, which is comparable with [C$_2$C$_1$Im][OAc]. Compared to EOA based ILs, ILs derived from DEOA, TEOA and TEA exhibited lower activities. A possible reason is the decrease of net basicity of IL and basicity of the base. The anion of PILs also exhibited obvious effect on the sugar yield. Among the anions, acetate was the best one. It was proposed that the type of acid was in charge of the acidic of PILs. Due to much higher acidity of sulfuric acid, hydrochloric acid and formic acid, the corresponding PILs exhibit much poor activities for the production of sugar. Based on the above discussion, [EOA] [OAc] was chosen as the model media for the further investigation.

Effect of Parameters on the Yield of Sugars

Thereafter, the effect of parameters on the sugar yields including temperature, time, biomass loading, IL concentration using switchgrass (SG) as the model biomass were studied systematically (FIGS. 4A-4D). FIG. 4A showed that although the increasing biomass loading in pretreatment process would lead to a decrease in sugar yield, more than 75% glucose could still be obtained with the biomass loading range from 5 to 20 wt %. Even at 25 wt % SG loading, around 60% glucose yield could be achieved. The above results proved a good pretreated ability of the [EOA][OAc] IL to SG.

It could be found that sugar yield was sensitive to the increasing of the pretreatment temperature in a range of 140 to 160° C. (FIG. 4B). At a 10% SG loading, a satisfactory sugar yield could be obtained using around 160° C. as the pretreatment temperature. Pretreatment at temperatures below 140° C. led to lower glucose yields, possibly because the pretreatment may not be severe enough to effectively overcome the biomass recalcitrance. Since the reported thermal decomposition temperature, $T_d$, of [EOA] [OAc] is above 200° C.[24,25] IL degradation is considered minimal. FIG. 4B also depicted the effect of pretreatment time on the sugar yield. In one-hour pretreatment process with a higher enzyme loading (20 mg protein/ g SG), it was proved that higher temperature could achieve higher sugar yield (160 vs. 150° C.). However, in a longer pretreatment time of 3 hrs, almost no change in sugar yield when increasing temperature from 150 and 160° C. The result indicated that 3 hrs is enough to eliminate the effect of temperature. But, compared to 140° C., the corresponding sugar yields were still increased. The result suggested that 140° C. may be a turning point of pretreatment temperature by using this kind of IL. In addition, at 160° C., almost no change on sugar yield with the varies of time, and above 80% glucose yield could be obtained with 0.5 h, which was possibly caused by a high efficiency at this temperature.

As well known, the enzymatic and microbial toxicity of imidazolium based ILs often requires extensive water washes to remove residual IL from pretreated biomass despite the effectiveness of IL (e.g. [C$_2$C$_1$Im][OAc]) at reducing the recalcitrance of lignocellulosic biomass. As a result, the associated IL recycling and wastewater treatment costs create significant economic and process engineering challenges for the commercial scale-up of this technology. In the present process, commercial cocktails of CTec2+HTec2 (9:1, v/v) could tolerant about 10 wt % IL in saccharification process (FIG. 4C). And the corresponding result was competitive to those in 5 or 0 wt % IL conditions, which indicated that [EOA] [OAc] is tolerant to commercial cocktails not only in pH match, but also in its low toxic nature.

After that, we test the applicability of [EOA] [OAc] for the pretreatment of different biomass. The biomass we selected are mixed feedstock (weight ratio of eucalyptus to SG=1:1), eucalyptus, and Corn Stover. The biomass were milled with 40 mesh before use. The corresponding results were summarized in FIG. 4D. It could be seen that among the biomass investigated, Corn Stover is the best one with the highest yield. The low sugar yields in the cases of mixed feedstock and eucalyptus might be caused by the high lignin content in the corresponding biomass.

Based on the above discussion, it was found that the temperature played an obvious effect on the pretreatment efficiency. In order to know the possible reason from the viewpoint of nature of biomass, composition analysis before and after pretreatment with different conditions using [EOA] [OAc] IL was studied and the results were summarized in Table 2. Solid recovery refers to the mass percentage of biomass (dry weight) recovered from the original biomass load. After washing, between 55 and 81% of the biomass was recovered. Generally, pretreatment under higher temperature conditions resulted in less solid recovery.[8] Three of the major plant cell wall components of SG, such as glucan, xylan, and acid insoluble lignin were monitored before and after pretreatment. Untreated SG contained 29.6% glucan, 18.4% xylan and 20% acid insoluble lignin (entry 1). After pretreatment, the glucan loading generally increased and higher temperature or longer time resulted in higher glucan contents in pretreated biomass. The exception was found when the temperature was reach up to 160° C., whereby the glucan contents were similar after treated for three time conditions from 0.5, 1 to 3 hrs (48.0 vs. 48.9 and 49.8%, respectively) (entries 6-8). However, xylan contents for pretreated biomass were not increased too much compared to those of the original biomass, varying within a range of around 24-27%. On the other hand, lignin content of pretreated material generally decreased as compared to the original biomass. This trend was most obvious after pretreatment under higher temperature where lignin content was reduced by 77% (untreated: 20% vs. pretreated: 4.7%). The removal or recovery of major components (X) was calculated based on the method described in our previous work.[8] Although the compositional changes do not always reflect the actual component recovery because of the different solid recovery, higher temperature IL pretreatment facilitated lignin removal. These results obtained with [EOA] [OAc] IL are consistent with our previous report by using basic ILs such as [Ch][Lys] and [C$_2$C$_1$Im][Lys].[8]

TABLE 2

Compositional analysis of switchgrass after [EOA][OAc] pretreatment.[a]

| T/t (° C./h) | Solid recovery/% | Glucan/% | Xylan/% | Lignin/% |
|---|---|---|---|---|
| —/— | — | 29.6 ± 0.1 | 18.4 ± 0.1 | 20.0 ± 0.1 |
| 120/1 | 80.67 | 40.6 ± 0.4 | 25.4 ± 0.2 | 11.6 ± 0.5 |
| 120/3 | 75.60 | 42.5 ± 0.7 | 26.0 ± 0.1 | 9.1 ± 1.8 |
| 140/1 | 65.03 | 48.2 ± 0.6 | 24.2 ± 1.1 | 8.4 ± 1.2 |
| 140/3 | 63.57 | 47.5 ± 0.1 | 24.0 ± 0.4 | 6.5 ± 0.4 |
| 160/0.5 | 56.17 | 48.0 ± 1.6 | 25.8 ± 0.6 | 6.1 ± 1.4 |
| 160/1 | 55.77 | 48.9 ± 1.6 | 26.6 ± 0.5 | 5.7 ± 1.6 |
| 160/3 | 55.37 | 49.8 ± 0.2 | 26.1 ± 0.9 | 4.7 ± 0.8 |

[a]Solid loading 10 wt %.

The proportions of crystalline/amorphous cellulose and the disordered components (i.e. amorphous cellulose, hemicelluloses and lignin) found in pretreated SG samples were determined by pXRD. The diffraction patterns of untreated SG and treated SG with 5 and 10 wt % biomass loading shows the following: Three similar peaks are observed in the diffraction patterns for all of the samples: the main peak position at 21.7° is indicative of the distance between hydrogen-bonded sheets in cellulose I; the broad peak at ~16° is known to be a composite of two peaks from $I_\beta$, $I_\alpha$, or both;[26] and the third small peak at 34.5° corresponds to ¼ of the length of one cellobiose unit and arises from ordering along the fiber direction.[27] Although SG pretreated with 100% [EOA][OAc] still retains primarily a cellulose I structure same with raw feedstock, small shift happened in the three peaks is an effect attributed to the removal of amorphous lignin, which is consistent with the result in Table 2. To further understand cellulose structural changes during pretreatment with [EOA][OAc], Avicel was pretreated under the same conditions and the XRD spectra is plotted. After pretreating Avicel in 100% [EOA][OAc], although cellulose I structure is still dominated as displayed in XRD patterns, the characteristic diffraction peak positions are little different from untreated Avicel (i.e. cellulose I and amorphous). It has been shown that anions play a critical role in cellulose solubilization, and those that accept hydrogen bonds from cellulose hydroxyl protons can effectively disrupt the inter- and intra-molecular hydrogen bonding in cellulose.[28] Also it is known that $[C_2C_1Im][OAc]$ is capable of dissolving or swelling cellulose. Although [EOA][OAc] has the same anion with $[C_2C_1Im][OAc]$, the difference in cation make a little effect on the crystalline structure change of cellulose. It might be caused by the strong inter-hydrogen bond formed by hydroxyl group in ammonium cation and the acetate anion, thus weakening the intra-hydrogen bond between IL and cellulose.

Integrated One-Pot SSF

Simultaneous saccharification and fermentation (SSF) after pretreatment is a frequent practice for cellulosic ethanol production recently. The presence of yeast together with the cellulolytic enzyme cocktail reduces the accumulation of sugars-therefore increasing yield and saccharification rate compared with separate saccharification and fermentation.[29] Another proposed advantage of this approach is a facilitate separation of IL from complicated sugar system. Our previous studies have demonstrated one successful high ethanol production from cellulosic biomass using SSF in the presence of basic IL.[30] However, pH adjustment is still a requirement for that case due to the basicity of IL.

Generally, SSF requires compatible fermentation and saccharification conditions, with a similar pH, temperature and optimum substrate concentration. In a case of IL participating SSF, a compromise IL concentration for the two stages is an accessional requirement. FIG. 4C shows that, in saccharification process, the use of commercial enzyme cocktails capable of hydrocarbon to sugar at a [EOA] [OAc] concentration of 10 wt %, however, increasing the [EOA] [OAc] concentration to over 10 wt % led to a decreased glucose yield. Thus, it would be interesting to see the performance of the wild yeast under different IL concentrations.

For toxicity screening, a wild type yeast strain BY4741 was technically used and it was immersed in various IL concentrations from 2.5 to 15 wt %. As shown in FIG. 5A, the IL concentration plays an important role for the yeast strain growth. A better growth occurs in a lower IL titer below 10 wt %. Since 5 wt % IL concentration could guarantee a better yeast growth, it was chosen as the optimal IL concentration during the current SSF.

FIG. 5B shows that 40 wt % starting biomass loading (i.e. 60 wt % IL) in pretreatment and then was diluted to a 5 wt % IL concentration in saccharification could generate a comparative glucose yield with 20 wt % starting biomass loading, which is favorite to a high capacity of biomass pretreatment based SSF process. Based on this result, 40 wt % starting biomass loading are therefore advisable when employing coupled SSF processes. Other conditions such as temperature and time as well as operation procedure were obtained from our previous work.

Based on the above results, performance of yeast in SSF was then investigated with different yeast inoculation varying from 0.01 to 0.5 wt %. FIG. 6A suggests that there is no significant difference in ethanol yield when the yeast loading increased from 0.01 to 0.21wt %. At pretty low yeast loading of 0.1 wt %, that is 1 g/L, around 70% of theoretical ethanol yield could be obtained. Under this conditions, the weight ratio of biomass feeding amount to yeast amount as high as around 33.3:1 indicating that the one-pot process is much efficient with high biomass loading. Under this conditions, FIG. 6B shows the dynamics of sugar consumption and ethanol production with the time. After two days, the ethanol yield reaches the top value.

Mass Balance

FIG. 7 described the glucan balances for the one-pot [EOA] [OAc] pretreatment and saccharification of switchgrass. By increasing the biomass loading, the one-pot process results in minimized IL usage as low as 1.5 kg/kg of biomass. In addition, this process realizes a yeast loading as low as 0.03 kg/kg of biomass. The glucan/glucose balance suggests over 90% of glucose from saccharification has been converted to ethanol, yielding an overall conversion of 70% in one-pot. As a result, 117 g ethanol was produced from the glucan present in 1 kg of switchgrass. In addition, the utilization the xylose in the hydrolysates could generate a more cost efficient process. For example, a microorganism that is capable of converting both glucose and xylose could utilize this concentrated sugar stream for improved biofuel yield. On the other hand, we did not determine the compounds such as proteins, sugar degradation products and other extractives herein.

Conclusions

In summary, we have developed a process in which a cheap pH matched ionic liquid was used instead of traditional imidazolium based ionic liquids. Without pH adjustment and washing operation, the pretreatment slurry could be directly used for the commercial enzyme saccharification process. The ionic liquids used are containing ions derived from simple amino bases (e.g., ethanolamine, diethanolamine, or triethanolamine choline) and acids (e.g., acetic acid, sulfuric acid, phosphoric acid, hydrochloric acid and formic acid). By optimizing the conditions of pretreatment and saccharification, ethanolamine acetate could pretreat biomass efficiently among the ionic liquids developed. As a result, an 85% glucose and 35% xylose (monomers) could be liberated from switchgrass by one-pot pretreatment and saccharification process. Also, a 70% ethanol yield could be achieved by simultaneous saccharification and fermentation process after pretreatment step. This current process establishes a new approach to affordable and scalable biomass conversion using efficient, and low cost IL under pH adjustment free and water washing free conditions.

Experimental Section

Switchgrass (SG) (Panicum virgatum) was provided by Dr. Daniel Putnam, University of California at Davis. Switchgrass was ground by a Wiley Mill through a 2 mm screen and separated by a vibratory sieve system (Endecotts, Ponte Vedra, Fla.). The SG fractions falling between 20 and 40 mesh were collected for use in this study and without drying. The SG contains 29.6%±0.01 glucan, 18.4%±0.01 xylan, 20.0%±0.01 lignin, 8.1%±0.01 $H_2O$ and 23.9% of other compounds remaining unidentified, on original basis. Microcrystalline cellulose (MCC, trademark name: Avicel) was purchased from Sigma-Aldrich (St. Louis, Mo.). The commercial enzyme products cellulase (Cellic® CTec2, Batch#VCN10001) and hemicellulase (Cellic® HTec2, Batch #VHN00001) were gifts from Novozymes, North America (Franklinton, N.C.).

Compositional analysis of SG before and after pretreatment was performed using NREL acidolysis protocols (LAP) LAP-002 and LAP-005, which was described in our previous work.[13] In a typical process, 200 mg of biomass and 2 mL of 72wt % $H_2SO_4$ were incubated at 30° C. while shaking at 300 rpm for 1 h. The solution was diluted to 4wt % $H_2SO_4$ with 56 mL of DI water and autoclaved for 1 h at 121° C. The reaction was quenched into an ice bath before removing the biomass by filtration. Carbohydrate concentrations were determined from the filtrate using an Agilent HPLC 1200 Series equipped with a Bio-Rad Aminex HPX-87H column and a Refractive Index detector. An aqueous solution of $H_2SO_4$ (4 mM) was used as the mobile phase (0.6 mL min$^{-1}$, column temperature 50° C.). The injection volume was 20 µL with a run time of 20 min. Acid insoluble lignin was quantified gravimetrically from the solid after heating overnight at 105° C. (the weight of acid-insoluble lignin+ash) and then at 575° C. for at least 6 h (the weight of ash).

One-pot pretreatment, saccharification and fermentation: In a typical procedure, SG (100 mg) was mixed with ([EOA][OAc]) at a 10% biomass loading in a 15 mL capped glass pressure tube and pretreated in a convection oven at 160° C. for 0.5 h. Untreated raw SG (30-40 mesh) was used as a control. After pretreatment, the pretreatment slurry was diluted with water to obtain a final IL concentration of 10 wt %. A CTec2+ HTec2 (9:1 v/v) mixture at 20 mg EP per g starting biomass was added to the pretreatment slurry. Enzymatic hydrolysis using CTec2+ HTec2 cocktail was conducted at 50° C. for 72 h, with constant agitation on an Enviro Genie SI-1200 rotator platform (Scientific Industries, Inc., Bohemia, N.Y.).

X-ray diffraction (XRD) and NMR spectroscopy: The raw and pretreated biomass were dried and characterized with powder X-ray diffraction (PXRD). The XRD analysis were performed on a PANalytical Empyrean X-ray diffractometer equipped with a PIXcel$^{3D}$ detector and operated at 45 kV and 40 kA using Cu Kα radiation (λ=1.5418 Å). The patterns are collected in the 2θ range from 5 to 60° with a step size of 0.039° and the exposure time of 300 seconds. A reflection-transmission spinner was used as a sample holder and the spinning rate was set at 8 rpm throughout the experiment. NMR spectra were acquired at 298 K using a Bruker Avance-600 MHz instrument in DMSO-d6 and calibrated with the corresponding DMSO peak (δH=2.50 ppm for $^1$H and δC=39.50 ppm for $^{13}$C).

References cited in Example 1:

1 H. Wang, G. Gurau and R. D. Rogers, *Chemical Society Reviews*, 2012, 41, 1519.
2 Mosier, C. Wyman, B. Dale, R. Elander, Y. Y. Lee, M. Holtzapple and M. Ladisch, *Bioresource Technol*, 2005, 96, 673.
3 J. P. Hallett and T. Welton, *Chemical Reviews*, 2011, 111, 3508.
4 J. Shi, V. S. Thompson, N. A. Yancey, V. Stavila, B. A. Simmons and S. Singh, *Biofuels*, 2013, 4, 63.
5 C. L. Li, D. Tanjore, W. He, J. Wong, J. L. Gardner, K. L. Sale, B. A. Simmons and S. Singh, *Biotechnology for Biofuels*, 2013, 6.
6 A. S. A. da Silva, R. S. S. Teixeira, T. Endo, E. P. S. Bon and S.-H. Lee, *Green Chemistry*, 2013, 15, 1991.
7 J. Shi, J. M. Gladden, N. Sathitsuksanoh, P. Kambam, L. Sandoval, D. Mitra, S. Zhang, A. George, S. W. Singer, B. A. Simmons and S. Singh, *Green Chem*, 2013, 15, 2579.
8 N. Sun, R. Parthasarathi, A. M. Socha, J. Shi, S. Zhang, V. Stavila, K. L. Sale, B. A. Simmons and S. Singh, *Green Chem*, 2014, 16, 2546.
9 L. Chen, M. Sharifzadeh, N. Mac Dowell, T. Welton, N. Shah and J. P. Hallett, *Green Chem*, 2014, 16, 3098.
10 K. Ohira, Y. Abe, M. Kawatsura, K. Suzuki, M. Mizuno, Y. Amano and T. Itoh, *ChemSusChem*, 2012, 5, 388.
11 L. C. Tomé, D. J. S. Patinha, R. Ferreira, H. Garcia, C. Silva Pereira, C. S. R. Freire, L. P. N. Rebelo and I. M. Marrucho, *ChemSusChem*, 2014, 7, 110.
12 Q.-P. Liu, X.-D. Hou, N. Li and M.-H. Zong, *Green Chem*, 2012, 14, 304.
13 Y. Fukaya, Y. Iizuka, K. Sekikawa and H. Ohno, *Green Chem*, 2007, 9, 1155.
14 X. L. Yuan, S. J. Zhang and X. M. Lu, *Journal of Chemical & Engineering Data*, 2007, 52, 596.
15 X. Yuan, S. Zhang, J. Liu and X. Lu, *Fluid Phase Equilibria*, 2007, 257, 195.
16 J. Sun, S. Zhang, W. Cheng and J. Ren, *Tetrahedron Letters*, 2008, 49, 3588.
17 L. Zhai, Q. Zhong, C. He and J. Wang, *Journal of Hazardous Materials*, 2010, 177, 807.
18 B. Guo, E. Duan, A. Ren, Y. Wang and H. Liu, *Journal of Chemical & Engineering Data*, 2009, 55, 1398.
19 G. Cui, C. Wang, J. Zheng, Y. Guo, X. Luo and H. Li, *Chemical Communications*, 2012, 48, 2633.
20 M. Ismail Hossain, M. El-Harbawi, Y. A. Noaman, M. A. B. Bustam, N. B. M. Alitheen, N. A. Affandi, G. Hefter and C.-Y. Yin, *Chemosphere*, 2011, 84, 101.
21 A. Brandt, J. P. Hallett, D. J. Leak, R. J. Murphy and T. Welton, *Green Chem*, 2010, 12, 672.
22 A. Parviainen, A. W. T. King, I. Mutikainen, M. Hummel, C. Selg, L. K. J. Hauru, H. Sixta and I. Kilpelainen, *Chemsuschem*, 2013, 6, 2161.
23 L. K. J. Hauru, M. Hummel, A. W. T. King, I. Kilpeläinen and H. Sixta, *Biomacromolecules*, 2012, 13, 2896.
24 K. A. Kurnia, C. D. Wilfred and T. Murugesan, *The Journal of Chemical Thermodynamics*, 2009, 41, 517.
25 T. L. Greaves, A. Weerawardena, C. Fong, I. Krodkiewska and C. J. Drummond, *J Phys Chem B*, 2006, 110, 26506.
26 M. Wada, T. Kondo and T. Okano, *Polym J*, 2003, 35, 155.

27 G. Cheng, P. Varanasi, C. Li, H. Liu, Y. B. Melnichenko, B. A. Simmons, M. S. Kent and S. Singh, *Biomacromolecules,* 2011, 12, 933.
28 R. C. Remsing, R. P. Swatloski, R. D. Rogers and G. Moyna, *Chemical Communications,* 2006, 1271.
29 C. E. Wyman and N. D. Hinman, *Appl Biochem Biotech,* 1990, 24-5, 735.
30 F. Xu, J. Sun, N. V. S. N. M. Konda, J. Shi, T. Dutta, C. D. Scown, B. A. Simmons and S. Singh, *Energy & Environmental Science,* 2016.

EXAMPLE 2

Rapid Room Temperature Solubilization and Depolymerization of Lignin at High Loading Rapid room temperature solubilization of lignin at high solid loadings (>30 wt %) can be easily achieved in a single step using the inexpensive solvent ethylene glycol (EG) followed by rapid lignin recovery in a fibrous shape with the addition of pure ethanol. The computational and nuclear magnetic resonance spectroscopy results confirm that strong hydrogen bond interactions between EG and the free hydroxyl groups present in lignin linkages contribute to the lignin dissolution. In addition, hydrogen peroxide mediated depolymerization of lignin in EG at low temperature (≤80° C.) was conducted, and is hypothesized to be similar to the mechanism of microbial lignin degradation. These initial findings present exciting opportunities to more deeply understand how hydrogen bond donors work in the potential for high lignin solubilization and valorization.

Introduction

As a primary component of lignocellulosic biomass, lignin has been typically underused and burned for generation of heat. Currently, there is a growing interest in the development of lignin-based value-added products as fuels, solvents, chemical reagents, and polymers for improving the economics of the lignocellulosic biorefinery.[1-2]

For effective valorization of lignin to occur, it is first essential to dissolve lignin in a relatively inexpensive and non-toxic solvent at high loading.[1] Solvation of lignin at higher loading levels is challenging because of its complex three-dimensional amorphous structure and heterogeneous composition. Although ionic liquids (ILs) have shown an improved lignin removal rate during the biomass pretreatment process as well as the ability to solubilize lignin at high temperature,[3-4] their low temperature performance in terms of lignin solubilization is not sufficient.[5] Lignin depolymerization with selective bond cleavage is another major challenge for converting lignin into value-added bioproducts. A variety of catalytic, thermal, and biological approaches have been employed to break lignin down to its constituent monomers, followed by conversion of the resulting monomers to bioproducts such as fuels or chemicals.[1,6-7] Biochemical lignin degradation is generally achieved via the action of peroxidases, laccases, and additional oxidative enzymes from fungi and bacteria, which produce aromatic radicals that cleave diverse lignin linkages through non-enzymatic reactions.[7] Inspired by this mechanism, novel lignin degradation methods could be developed.

Liquefaction of chitin, cellulose and biomass in acidified high boiling organic solvents such as ethylene glycol (EG) and/or ethylene carbonate (EC) have been reported.[8-13] The economic viability of this approach is challenging due to the requirements of high temperature (e.g. >200° C.), and a relatively high solvent/substrate ratio that is typically greater than 10:1.[9] To date, very limited research has been carried out on the dissolution capacities and depolymerization efficiencies of lignin in high boiling solvents such as EG, EC, propylene carbonate, and poly(ethylene glycol). Here we report that EG, an inexpensive, relatively non-toxic solvent, can solubilize a large amount of lignin at room temperature, and that the solubilized lignin can be easily recovered by using a relatively inexpensive anti-solvent such as ethanol. In addition, we found that the solubilized lignin can be further depolymerized in situ using hydrogen peroxide at low temperature. Based on these results, nuclear magnetic resonance spectroscopy and computational modeling were used to explore the corresponding solubilization and depolymerization mechanism.

Result and Discussions

Lignin Solubilization

Alkali lignin (average molecular weight of lignin obtained from Sigma-Aldrich reported as 60.0 kDa) with low sulfonate content was used as a technical lignin substrate for the rapid solubilization experiments. As reported in Table 3, approximate 31 wt % lignin can be solubilized using EG as a solvent (Table 3, entry 1). Compared to EG, only 1 wt % lignin can be dissolved in 1-ethyl-3-methyl imidazolium acetate ([$C_2C_1$Im][OAc]) at room temperature (entry 2). If the process is carried out at 80° C., only 18 wt % of lignin can be dissolved in the same IL (entry 3), which indicates the efficiency of EG in solubilization of lignin as compared to the commonly used IL. We also investigated lignin solubilization using low molecular weight polyethylene glycol (PEG). For example, using PEG with molecular weight of 200 or 400 (PEG 200 and PEG 400; entries 4 and 5) as the solvents, much lower solubilities were observed as compared to those observed in EG. We hypothesize that this result can be attributed to the relatively high viscosity of PEG[14] and its weak hydrogen bond network as compared to EG. Glycerol achieved approximately 25 wt % solubilization (entry 6). The more rapid and higher amount of lignin dissolution in EG might be related to its lower viscosity (0.0162 N s/m², 25° C.) as compared to glycerol (0.95 N s/m², 25° C.). Negligible solubility was detected in the case of solvents such as ethylene carbonate (EC), propylene carbonate (PC), and ethanol at room temperature (entries 7-9). The above results indicate that EG is a very effective lignin solvent at 25° C. and at high loading (>30 wt %), and this might be caused by the formation of strong hydrogen bond interactions between EG and hydroxyl group of lignin molecules.

TABLE 3

Effect of solvent on the solubilization of alkali lignin.[a]

| Entry | Solvents | Temperature (° C.) | Solubility (wt %)[b] |
|---|---|---|---|
| 1 | EG | 20 | 31 |
| 2 | [$C_2C_1$Im][OAc] | 20 | 1 |
| 3 | [$C_2C_1$Im][OAc] | 80 | 18 |
| 4 | PEG200 | 20 | 2 |
| 5 | PEG400 | 20 | 1 |
| 6 | Glycerol | 20 | 25 |
| 7[c] | EC | 50 | Trace |
| 8 | PC | 20 | Trace |
| 9 | Ethanol | 20 | Insoluble |

[a]Conditions: solvent 5 g, 20° C.;
[b]Solubility was determined by using VWR Vista Vision Stereo Microscope with 20 X magnification.

FIGS. 8A-8F describes the processes of rapid dissolution and separation of lignin at room temperature. We found that at room temperature (~20° C.), >30 wt % lignin can be completely dissolved in EG (FIG. 1A) using a vortex mixer (1000 rpm) and generates a dark, highly viscous solution (FIG. 1B). Most of the dissolved lignin can be precipitated immediately by using anhydrous ethanol as an anti-solvent (FIG. 8C) and can be easily recovered via centrifugation. Confocal microscopy (10× magnification) was used to observe the morphologies of lignin before and after solubilization and precipitation, and the results are shown in FIGS. 8D-8F. The fluorescence resulting from lignin particles can be seen under laser light at an excitation wavelength of 543 nm, and approximately circular particles were observed at low magnification (FIG. 1D). After solubilization in EG, a homogenous system with strong fluorescence (FIG. 1E) and no visible particles was observed. Interestingly, after adding ethanol as the anti-solvent, fibrous fluorescence related to lignin precipitates were observed (FIG. 1F).

Determining the Mechanism of Lignin Solubilization

As mentioned previously, EG demonstrates extraordinary properties for lignin dissolution compared to the other organic solvents considered in this investigation. The interactions between EG and lignin are not well understood. Therefore, an examination of the structure and stability of EG complexes with a lignin-like small molecule containing a β-O-4 linkage, guaiacylglycerol-β-guaiacyl ether (mixture of erytho and threo), or dilignol, was used to further understand the relationship between the hydrogen bond interactions and solvation properties of EG at the molecular level.

Several different molecular conformations and geometries are possible for the dilignol-EG interaction owing to the structural flexibility of EG and dilignol. To obtain the most stable structures of the dilignol-EG complex, many starting complexes were considered based on intermolecular hydrogen bonding between EG molecules and the hydroxyl groups of dilignol. Fifteen initial geometries were considered in each case and optimized at the M06-2X/6-31+G (d, p) level of theory. Harmonic frequencies at the same level of theory were calculated to ensure that the clusters were true minima. The most stable structures of dilignol-EG were classified according to the interaction of EG with 1) the α-C hydroxyl group, 2) the γ-C hydroxyl group and 3) the phenolic hydroxyl group. These complexes were optimized at higher level M06-2X/6-311+G (2d, 2p) level of theory using the G09 suite of programs.[15]

IEs were calculated using a supermolecular approach and corrected for basis set superposition error (BSSE) using the counterpoise (CP) procedure suggested by Boys and Bernardi,[15] which equation is provided below:

$$IE = -\left(E_{Complex} - \left(\sum_{i=1}^{m} E_{Lignol} + \sum_{j=1}^{n} E_{EG_j}\right)\right) \quad (1)$$

where $E_{complex}$ refer to the total energies of dilignol with EGs and $E_{lignol}$ and $E_{EGj}$ are the total energies of the dilignol and EG, respectively.

The geometries of the dilignol-EG complexes optimized at the M06-2X/6-311++G (2d, 2p) level of theory are presented in FIGS. 8A-8H, along with their hydrogen bond distances. Both hydroxyl groups of EG molecules can donate and accept hydrogen bonds with dilignol hydroxyl groups simultaneously. Some of the vibrational frequencies of individual molecules undergo substantial shifts and changes in the frequencies provide information about the characteristics of interaction between molecules. A red shift in the —OH stretching frequencies has been used to characterize hydrogen bond formation. Therefore, vibrational frequencies for isolated lignin OH groups and their interaction with EG have been calculated at same level. The calculated (scaled) frequency of individual lignol ring OH is 3710 and γ-OH is 3741 cm$^{-1}$ and in lignol-EG complexes, the calculated $v_{OH}$ stretches occur at 3483 and 3581 cm$^{-1}$, respectively. The red shifts of these modes from those of isolated phenol are 227 and 160 cm$^{-1}$, respectively, indicating the involvement of —OH groups in strong hydrogen bonds formed in lignin solvation by EG. The complex with EG interacting with the dilignol γ-C hydroxyl group (FIG. 8B vs. FIGS. 8A-B) is the most stable, with a cyclic intermolecular hydrogen bond network involving the hydroxyl group and the ether bond oxygen atom. There is a steady increase in the IE present in complexes of dilignol with two and three EG molecules (FIGS. 2D-E). In order get a more relevant model to experimental lignin dissolution in EG, a complex containing ten EG molecules (60%) solvating the dilignol (40%) was investigated (FIG. 2F). The optimization carried out using B3LYP/6-31G* in Terachem and single point calculations at M06-2X/6-311+G (2d, 2p) level of theory used get IE of the complex. FIG. 2F shows that the ten EG molecules completely solvated the dilignol by forming an intermolecular hydrogen bonding network. The calculated IEs indicate cooperativity in hydrogen bonding on the solvation of lignin by EG. Also, it is hypothesized that in these complexes, both electrostatic and polarization interactions are the predominant determinants of the structural properties of dissolution, and that dynamic properties are primarily influenced by the viscosity of the polar EG solvent.

It has been proposed that the interaction of IL (i.e. 1-allyl-3-methylimidazolium chloride) with lignin is stronger than that of lignin with lignin; thus lignin can be dissolved in IL.[16] To get a better understanding of the interactions between non-IL solvent (i.e. EG) and lignin, the effect of EG on the proton chemical shifts of lignin was investigated using NMR spectroscopy. The chemical shift assignments of the dilignol (FIG. 2G) were made using 2-D$^1$H-$^1$H COSY, $^1$H-$^{13}$C HSQC and HMBC experiments. Putative sites on the dilignol molecule that participate in the interaction with EG were identified from chemical shift perturbations during titration of EG into the dilignol solution. The effect of EG concentration on the shielding or deshielding of hydoxyl and phenolic protons in dilignol is shown in FIG. 2H. The proton of the phenolic hydroxyl group, which is the most acidic proton in the dilignol, demonstrates the greatest upfield shift with increasing EG concentration as compared to the other dilignol protons. This is contrary to the expected downfield shift due to formation of a hydrogen bond. However, at 0% EG concentration there is could be a strong intermolecular hydrogen bond between the O-atom of one phenolic-hydroxyl group of one dilignol molecule with the acidic proton of the phenolic hydroxyl group of another dilignol molecule.

In the presence of EG, these strong intermolecular hydrogen bonds between the dilignol molecules are replaced by relatively weaker hydrogen bonds between H-atom of phenolic-hydroxyl group and O-atom of an EG molecule. This replacement of the relatively strong H-bond of phenolic hydroxyl group in the dilignol dimer by a weaker H-bond in the dilignol-EG complex is reflected in a strong upfield shift of the phenolic hydroxyl proton. A downfield shift was observed for the γ-hydroxyl proton, suggesting relatively strong hydrogen bond between the γ-hydroxyl proton of dilignol and EG. These observations agree well with the theoretically predicted intermolecular dilignol-EG H-bond.

To compare the influence of EG interactions with dilignol, the bare dilignol and dilignol from the complexes were superimposed (FIG. 10) to gain insights into the overall influence of the geometrical variations (root mean square deviations, RMSD). We carried out calculations on a water molecule interacting with dilignol and a $H_2O_2$ interacting with dilignol-$EG_1$ complex and structural changes were analyzed. The dilignol structures are not much influenced by water (0.3 Å) interactions, but $EG_1$ induced noticeable variation in dilignol conformations. Likewise, dilignol from $EG_3$ and $EG_1$-$H_2O_2$ also underwent more conformational changes from bare dilignol than dilignol in water. FIG. 10 also shows the superimposed model of the dilignol-$EG_{10}$; it indicates that there is significant variation on the conformation from the bare dilignol to this complex. This observation suggests that the dilignol conformation is affected by the hydrogen bond interactions of EG molecules, and that overall EG solvation changes the viscoelastic properties of lignin at room temperature, which could be the possible reason for the prominent solubility.

Depolymerization of Solubilized Lignin

After establishing the favorable lignin solvation properties of EG, we explored the depolymerization of lignin in EG medium. As literature reports that acidic conditions are beneficial for biomass liquefaction, a non-toxic acidic gas, carbon dioxide ($CO_2$), was employed, instead of corrosive sulfuric acid, since $CO_2$ has been used for pretreating lignocellulosic biomass,[17-18] and is easily removed. The polydispersity of depolymerized lignin was determined by using size exclusion chromatography UV-A absorbance (SEC UV-A300) as previously described.[19-20]

The effect of different temperatures, ranging from room temperature (20° C.) to 160° C., the temperature frequently used for [$C_2C_1$Im][OAc], was investigated in the presence of $CO_2$ (2 MPa) in order to explore the feasibility of low temperature depolymerization of lignin. The original alkali lignin and the dissolved alkali lignin in EG at room temperature were selected as the controls. There is almost no change on the alkali lignin before and after it is dissolved in EG at room temperature. With increasing temperature, the typical peak of original alkali lignin appeared centered at 10.30 min, slightly shifted from 10.35 to 10.40 min, which indicated that some breakdown of lignin into smaller fragments occurred but that most of the lignin still remained as very large molecules not affected by EG treatment even at 160° C. Depolymerization of alkali lignin could be observed at 80° C., where a peak centered at 11.30 min in the original lignin clearly shifted to 11.80 min. The small degree of polymerization of lignin might be caused by the acidic condition provided by the formation of carbonic acid in situ.

Since the pH of the system in the presence of $CO_2$ drops with the decrease in temperature, we carried out depolymerization experiments at temperatures below 80° C. in order to obtain optimal depolymerization. As expected, a new peak centered at 12.3 min appeared and became more obvious with the further decrease of the temperature, indicating that much more lignin was depolymerized into small fragments with the drop of pH. The best result could be observed at room temperature. For comparison, we employed other agents such as acidic resins (e.g. Amberlyst 15, and Dowex 50 WX4) and [$C_2C_1$Im][OAc] IL for the depolymerization of alkali lignin. In the case of acidic resins, water was used as the solvent and the operation conditions were 100° C. and 3 h. 160° C. and 3 h were used for [$C_2C_1$Im][OAc] based on our previous results.[21-22] However, a lower degree of depolymerization was observed in those cases. The results indicated that the depolymerization efficiency of EG/$CO_2$ system is higher than acidic resins and comparable with [$C_2C_1$Im][OAc].

Next, $H_2O_2$ (30 wt %) was introduced into the system instead of $CO_2$ for the depolymerization of lignin at a temperature range of 20 to 80° C. A β-O-4 model dilignol and vanillyl alcohol (monolignol) as well as original alkali lignin were used as reference for the SEC analysis. FIG. 11 showed that new peaks centered between 18.5 to 20.5 min could be observed. Almost no effect of the temperature on the depolymerization profiles was found within one hour. However, two separate peaks with comparable retention time with β-O-4 dimer and vanillyl alcohol could be distinguished at 80° C. for 4 h.

The oxidative action of the $H_2O_2$ derived radicals is thought to contribute to lignin depolymerization by fragmenting the lignin macrostructure into a number of low molecular weight compounds.[23] However, this corresponding process is too complex to be understood without considerable effort. Thus, β-O-4 phenolic dimer, a representative model for the dominant lignin substructure, was used to compare the depolymerization products from lignin. In our EG/$H_2O_2$ system, it was also hypothesized that lignin depolymerization follows a peroxidative cleavage mechanism, which is similar to previous studies on the degradation of lignin in the presence of $H_2O_2$.[24-25] The depolymerization products were identified by 15 Tesla Fourier transform ion cyclotron resonance mass spectrometry (FTICR-MS) and GC-MS. It can be observed from FIG. 12A that vanillic acid and guaiacol are the primary products derived from β-O-4 phenolic dimer in this oxidation process, (FIG. 12B). It is interesting to find a higher selectivity of vanillic acid in the presence of EG, possibly because EG improves the solubility of lignin in the $H_2O_2$ aqueous system.

Computational Modelling of Lignin Depolymerization

The observation of vanillic acid and guaiacol among the reaction products prompted us to probe the molecular level details of the depolymerization reactions of EG-solvated lignin in the presence of $H_2O_2$. The reactions and products are akin to lignin degradation by fungal and bacterial systems.[26-29] In fungal ligninases (peroxidative cleavage), a single electron transfer (SET) charge transport process is involved in the production of cation radicals that induce degradation by cleaving lignin linkages.[30] Another study shows that bacterial strains convert coniferyl alcohol to intermediates coniferylaldehyde, ferulic acid, vanillic acid and finally to protocatechuic acid.[31] Multi step lignin degradation pathways have been demonstrated in biotic environments and these require multiple enzymes with a variety of cofactors.[32] To determine the factors involved in the bio-mimicking reactions on an abiotic system, the charge transfer analyses and bond dissociation energy profiles involved in the initiation of the dilignol-$EG_1$-$H_2O_2$ complexes were studied in detail. The natural bond orbital (NBO) approach is a convenient means to understand the donor-acceptor interaction and to decompose the various important interactions present in the hydrogen bond complexes, including the charge transfer (CT) component which is associated with partial electron transfer.[33-34] The NBO second-order interaction energies 3 are calculated and listed in Table 2 for dilignol (γ-C—OH)-$EG_1$ and dilignol (γ-C—OH)-$EG_1$-$H_2O_2$. Atom numbering of these complexes and fragments used for NBO analysis. It can be seen that every single hydrogen bond has a second-order interaction energy contributing to the stability of the complexes.

The interaction, n(O)→σ*(O—H), describes the partial CT or donor-acceptor interaction between the non-bonding orbital (lone pair) of the O atom and the anti-bonding orbital of the O—H. As expected, for each interaction, there is a considerable amount of partial electron transfer from n(O) to σ*(O—H). For the dilignol-EG$_1$, the sum of partial CT interaction is 17.9 kcal/mol. The respective CT interaction for dilignol (γ-C—OH)-EG$_1$-H$_2$O$_2$ is 44.23 kcal/mol. It is interesting to note that CT interaction energy of dilignol (fragment 1) to EG (fragment 2) is higher for dilignol (γ-C—OH)-EG$_1$-H$_2$O$_2$ than for dilignol-EG$_1$. The CT interaction energy in dilignol (γ-C—OH)-EG$_1$-H$_2$O$_2$ from EG (fragment 2) to H$_2$O$_2$ is 19.18 kcal/mol and in the H$_2$O$_2$ (fragment 3) to dilignol (fragment 1) is 8.33 kcal/mol. These variations clearly indicate that each CT interaction is different and that CT interactions in dilignol-EG$_1$ contribute to the stability of the solvated complexes. On the other hand, it is evident from the significant CT interactions in dilignol (γ-C—OH)-EG$_1$-H$_2$O$_2$ complexes that presence of H$_2$O$_2$ increases the CT from dilignol to EG to H$_2$O$_2$ to dilignol and that this could be one of the main factors contributing to lignin dissociation in the presence of H$_2$O$_2$. The weakening of lignin linkages upon H$_2$O$_2$ interactions destabilizes the C—C and C—O bonds, initiates the bond breaking reactions] to form guaiacol intermediates including ferulic acid and, upon further decomposition, vanillic acid. These biomimicking chemical catalytic routes are powerful compared to biotic systems to date and hydroxylation, decarboxylation or demethylation reactions of various sites could serve to generate new chemical handles for future market demands.

TABLE 4

Donor orbitals ($\varphi_i$), acceptor orbitals ($\varphi_j$), and the corresponding second-order interaction energies of dilignol-EG$_1$ (γ-C—OH) and dilignol-EG$_1$ (γ-C—OH)—H$_2$O$_2$ complexes.

| System | Fragment | $\phi_i \rightarrow \phi_j$ | $\Delta E_{ij}^{(2)}$ kcal/mol |
|---|---|---|---|
| Dilignol-EG$_1$ (γ-C—OH) | Fragment 1 to 2 | n(O)15→σ*(O10—H52) | 3.47 |
|  |  | n(O)26→σ*(O51—H53) | 4.56 |
|  | Fragment 2 to 1 | n(O)50→σ*(O26—H27) | 9.87 |
| Dilignol-EG$_1$ (γ-C—OH)—H$_2$O$_2$ | Fragment 1 to 2 | n(O)26→σ*(O51—H53) | 7.74 |
|  |  | n(O)38→σ*(O50—H52) | 7.52 |
|  | Fragment 2 to 3 | n(O)50→σ*(O54—H57) | 19.2 |
|  | Fragment 3 to 1 | n(O)55→σ*(O26—H27) | 8.33 |

Conclusions

Rapid room temperature solubilization of lignin at >30 wt % solid loading was achieved using ethylene glycol (EG). The results indicated that both hydroxyl groups of EG molecule can donate and accept hydrogen bonds with dilignol hydroxyl groups simultaneously. $^1$HNMR spectra demonstrated that the proton of the phenolic-hydroxyl group, which is the most acidic proton in the dilignol, experiences the greatest upfield shift (suggesting H-bond donor interactions) with increasing EG concentration as compared to the other dilignol protons. EG interactions with the γ-C hydroxyl group present in dilignol is the most stable complex observed, with a cyclic intermolecular hydrogen bond network involving the hydroxyl group and the ether bond oxygen atom. The addition of ethanol promotes the fast precipitation of lignin from EG after dissolution. Monomeric lignin products such as vanillic acid and guaiacol derived from the depolymerization of lignin in a mixed EG and H$_2$O$_2$ system under low temperature were observed. This combined process of solubilization and depolymerization is a very effective route of breaking down lignin into targeted monomers that may enable the production of biofuels and bioproducts within a biorefinery setting.

References Cited in Example 2:

1 J. Zakzeski, P. C. A. Bruijnincx, A. L. Jongerius and B. M. Weckhuysen, Chem Rev, 2010, 110, 3552.
2 T. J. Morgan and R. Kandiyoti, Chem Rev, 2014, 114, 1547.
3 G. Cheng, X. Zhang, B. Simmons and S. Singh, Energy & Environmental Science, 2015, 8, 436.
4 N. Sun, R. Parthasarathi, A. M. Socha, J. Shi, S. Zhang, V. Stavila, K. L. Sale, B. A. Simmons and S. Singh, Green Chemistry, 2014, 16, 2546.
5 Y. Q. Pu, N. Jiang and A. J. Ragauskas, Journal of Wood Chemistry and Technology, 2007, 27, 23.
6 A. J. Ragauskas, G. T. Beckham, M. J. Biddy, R. Chandra, F. Chen, M. F. Davis, B. H. Davison, R. A. Dixon, P. Gilna, M. Keller, P. Langan, A. K. Naskar, J. N. Saddler, T. J. Tschaplinski, G. A. Tuskan and C. E. Wyman, Science, 2014, 344, 709.
7 G. T. Beckham, C. W. Johnson, E. M. Karp, D. Salvachúa and D. R. Vardon, Curr Opin Biotech, 2016, 42, 40.
8 T. Zhang, Y. Zhou, D. Liu and L. Petrus, Bioresource Technology, 2007, 98, 1454.
9 E. Jasiukaitytė, M. Kunaver and M. Strlič, Cellulose, 2009, 16, 393.
10 A. Krzan and E. Zagar, Bioresource Technology, 2009, 100, 3143.
11 D. H. Lee, E. Y. Cho, C. J. Kim and S. B. Kim, Biotechnology and Bioprocess Engineering, 2010, 15, 1094.
12 Y. Pierson, X. Chen, F. D. Bobbink, J. G. Zhang and N. Yan, Acs Sustainable Chemistry & Engineering, 2014, 2, 2081.
13 Z. Zhang, I. M. O'Hara, D. W. Rackemann and W. O. S. Doherty, Green Chemistry, 2013, 15, 255.
14 N. V. Zivkovic, S. S. Serbanovic, M. L. Kijevcanin and E. M. Zivkovic, Journal of Chemical and Engineering Data, 2013, 58, 3332.
15 S. F. Boys and F. Bernardi, Mol Phys, 2002, 100, 65.
16 W. Y. Ji, Z. D. Ding, J. H. Liu, Q. X. Song, X. L. Xia, H. Y. Gao, H. J. Wang and W. X. Gu, Energy & Fuels, 2012, 26, 6393.
17 J. S. Luterbacher, J. W. Tester and L. P. Walker, Biotechnology and Bioengineering, 2012, 109, 1499.
18 J. S. Luterbacher, J. W. Tester and L. P. Walker, Biotechnology and bioengineering, 2010, 107, 451.
19 A. George, K. Tran, T. J. Morgan, P. I. Benke, C. Berrueco, E. Lorente, B. C. Wu, J. D. Keasling, B. A. Simmons and B. M. Holmes, Green Chemistry, 2011, 13, 3375.
20 N. Sathitsuksanoh, K. M. Holtman, D. J. Yelle, T. Morgan, V. Stavila, J. Pelton, H. Blanch, B. A. Simmons and A. George, Green Chemistry, 2014, 16, 1236.

21 J. Shi, J. M. Gladden, N. Sathitsuksanoh, P. Kambam, L. Sandoval, D. Mitra, S. Zhang, A. George, S. W. Singer, B. A. Simmons and S. Singh, *Green Chemistry*, 2013, 15, 2579.
22 S. Singh, G. Cheng, N. Sathitsuksanoh, D. Wu, P. Varanasi, A. George, V. Balan, X. Gao, R. Kumar, B. Dale, C. Wyman and B. Simmons, *Frontiers in Energy Research*, 2015, 2.
23 M. J. Selig, T. B. Vinzant, M. E. Himmel and S. R. Decker, *Applied Biochemistry and Biotechnology*, 2009, 155, 397.
24 T. K. Kirk and R. L. Farrell, *Annual Reviews in Microbiology*, 1987, 41, 465.
25 H. B. Zhu, Y. M. Chen, T. F. Qin, L. Wang, Y. Tang, Y. Z. Sun and P. Y. Wan, *Rsc Advances*, 2014, 4, 6232.
26 K.-E. L. Eriksson, R. Blanchette and P. Ander, *Microbial and enzymatic degradation of wood and wood components*, Springer Science & Business Media, 2012.
27 T. Higuchi, in *New Trends in Research and Utilization of Solar Energy through Biological Systems*, eds. H. Mislin and R. Bachofen, Birkhäuser Basel, Basel, 1982, pp. 87-94.
28 M. E. Brown, M. C. Walker, T. G. Nakashige, A. T. Iavarone and M. C. Y. Chang, *J Am Chem Soc*, 2011, 133, 18006.
29 T. D. H. Bugg, M. Ahmad, E. M. Hardiman and R. Rahmanpour, *Nat Prod Rep*, 2011, 28, 1883.
30 D. W. Cho, R. Parthasarathi, A. S. Pimentel, G. D. Maestas, H. J. Park, U. C. Yoon, D. Dunaway-Mariano, S. Gnanakaran, P. Langan and P. S. Mariano, *J Org Chem*, 2010, 75, 6549.
31 L. Eggeling and H. Sahm, *Arch Microbiol*, 1980, 126, 141.
32 T. D. H. Bugg, M. Ahmad, E. M. Hardiman and R. Singh, *Curr Opin Biotech*, 2011, 22, 394.
33 A. E. Reed, L. A. Curtiss and F. Weinhold, *Chem Rev*, 1988, 88, 899.
34 R. Parthasarathi, V. Subramanian and N. Sathyamurthy, *Synth React Inorg Me*, 2008, 38, 18.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method for dissolving and depolymerizing lignin comprising: (a) providing a composition comprising lignin, (b) contacting the composition with a strong hydrogen donor and an ionic liquid (IL) to form a first solution, (c) incubating the first solution at a temperature less than 80° C., whereby at least 20% by weight of the lignin is dissolved, (d) introducing an oxidation agent to the first solution to form a second solution, wherein the temperature of the second solution is equal to or less than 100° C., whereby lignin is at least partly or wholly depolymerized, and (e) optionally introducing an anti-solvent to the second solution to precipitate the depolymerized lignin.

2. The method of claim 1, wherein the composition is a biomass comprising lignin.

3. The method of claim 1, wherein the composition of step (a) comprises a high solid loading whereby the composition comprises equal to or more than 10% by weight of a solid comprising the lignin.

4. The method of claim 1, wherein the strong hydrogen donor is a polyol.

5. The method of claim 4, wherein the polyol is an alkyl polyol.

6. The method of claim 5, wherein the alkyl polyol has an alkyl chain of 10 or fewer carbon atoms.

7. The method of claim 5, wherein the alkyl polyol is ethylene glycol (EG), propylene glycol, or glycerin (glycerol).

8. The method of claim 1, wherein the second solution has, or is incubated at, a temperature of equal to or less than 90° C.

9. The method of claim 8, wherein the second solution has, or is incubated at, a temperature of equal to or less than 80° C.

10. The method of claim 9, wherein the first solution and the second solution each have, or is incubated at, a temperature of equal to or less than 80° C. and more than 20° C.

11. The method of claim 10, wherein the first solution and the second solution each have, or is incubated at, a temperature of equal to or less than 70° C. and more than 20° C.

12. The method of claim 1, wherein step (c) results in the dissolution of at least 25% by weight of the lignin.

13. The method of claim 1, wherein the oxidation agent is hydrogen peroxide, $HNO_3$, $Br_2$, $IO_3^-$, $CrO_4^-$, $Pt^{2+}$, $MnO_2$, $O_2$, $Cr_2O_7^{2-}$, $Cl_2$ (g), $PbO_2$, $MnO_4^-$, $Co^{3+}$, $S_2O_8^{2-}$, $O_3$ (g), or $F_2$ (g).

14. The method of claim 1, wherein the method comprises (e) introducing an anti-solvent to the second solution to precipitate the depolymerized lignin.

15. The method of claim 14, wherein the anti-solvent is ethanol or isopropanol.

* * * * *